US006361951B1

(12) United States Patent
Thorp et al.

(10) Patent No.: US 6,361,951 B1
(45) Date of Patent: Mar. 26, 2002

(54) ELECTROCHEMICAL DETECTION OF NUCLEIC ACID HYBRIDIZATION

(75) Inventors: H. Holden Thorp, Chapel Hill, NC (US); Dean H. Johnston, Columbus, OH (US); Mary E. Napier, Carrboro, NC (US); Carson R. Loomis, Durham, NC (US); Mark F. Sistare, Chapel Hill, NC (US); Jinheung Kim, Kyungnam (KR)

(73) Assignee: The University of North Carolina at Chapel Hill, Chapel Hill, NC (US)

(*) Notice: Subject to any disclaimer, the term of this patent is extended or adjusted under 35 U.S.C. 154(b) by 0 days.

(21) Appl. No.: 09/603,217

(22) Filed: Jun. 26, 2000

Related U.S. Application Data

(60) Division of application No. 09/179,665, filed on Oct. 27, 1998, now Pat. No. 6,132,971, which is a division of application No. 08/667,338, filed on Jun. 20, 1996, now Pat. No. 5,871,918, which is a continuation-in-part of application No. 08/495,817, filed on Jun. 27, 1995, now abandoned.
(60) Provisional application No. 60/016,265, filed on Apr. 19, 1996, and provisional application No. 60/060,949, filed on Jun. 27, 1995.

(51) Int. Cl.[7] .......................... C12Q 1/68; C07H 21/02; A61B 5/05

(52) U.S. Cl. .......................... 435/6; 536/23.1; 600/345; 935/77; 935/78

(58) Field of Search ...................... 435/6, 91.2; 536/27, 536/28, 29; 546/2

(56) References Cited

U.S. PATENT DOCUMENTS

| | | | |
|---|---|---|---|
| 4,545,382 A | 10/1985 | Higgins et al. | 128/635 |
| 4,683,195 A | 7/1987 | Mullis et al. | 435/6 |
| 4,683,202 A | 7/1987 | Mullis | 435/91 |
| 4,704,535 A | 11/1987 | Humphries et al. | 435/4 |
| 4,800,159 A | 1/1989 | Mullis et al. | 435/172.3 |
| 4,840,893 A | 6/1989 | Hill et al. | 435/6 |
| 4,883,579 A | 11/1989 | Humphries et al. | 204/403 |
| 4,908,307 A | 3/1990 | Rodland et al. | 435/6 |
| 4,945,045 A | 7/1990 | Forrest et al. | 435/25 |
| 4,963,815 A | 10/1990 | Hafeman | 324/715 |
| 4,965,188 A | 10/1990 | Mullis et al. | 435/6 |
| 5,066,372 A | 11/1991 | Weetall | 204/153.1 |
| 5,108,889 A | 4/1992 | Smith | 435/4 |
| 5,112,974 A | 5/1992 | Barton | 546/4 |
| 5,143,854 A | 9/1992 | Pirrung et al. | 436/518 |
| 5,149,630 A | 9/1992 | Forrest et al. | 435/7.9 |
| 5,157,032 A | 10/1992 | Barton | 514/185 |
| 5,171,853 A | * 12/1992 | Thorp et al. | 536/27 |
| 5,175,082 A | 12/1992 | Jeffreys | 435/6 |
| 5,194,372 A | 3/1993 | Nagai et al. | 435/6 |
| 5,272,056 A | 12/1993 | Burrows et al. | 435/6 |
| 5,278,043 A | 1/1994 | Bannwarth et al. | 536/23.1 |
| 5,312,527 A | 5/1994 | Mikkelsen et al. | 204/153.12 |
| 5,378,628 A | 1/1995 | Grätzel et al. | 435/288 |
| 5,405,783 A | 4/1995 | Pirrung et all | 436/518 |
| 5,439,829 A | 8/1995 | Anderson et al. | 436/518 |
| 5,532,129 A | 7/1996 | Heller | 435/6 |
| 5,541,113 A | 7/1996 | Siddigi et al. | 436/56 |
| 5,545,531 A | 8/1996 | Rava et al. | 435/6 |
| 5,565,322 A | 10/1996 | Heller | 435/6 |
| 5,605,662 A | 2/1997 | Heller et al. | 422/68.1 |
| 5,632,957 A | 5/1997 | Heller et al. | 422/68.1 |
| 5,744,305 A | 4/1998 | Fodor et al. | 435/6 |
| 5,874,219 A | 2/1999 | Rava et al. | 435/6 |

FOREIGN PATENT DOCUMENTS

| | | | |
|---|---|---|---|
| EP | 0 478 319 | 4/1992 | |
| GB | 0478319 A | * 4/1992 | 435/6 |
| JP | 3076600 | 4/1992 | |
| WO | WO 85/02627 | 6/1985 | |
| WO | WO 91/15768 | 10/1991 | |
| WO | WO93/20230 | 10/1993 | |
| WO | WO 94/22889 | 10/1994 | |
| WO | WO 95/00530 | 1/1995 | |
| WO | WO 97/02359 | 1/1997 | |

OTHER PUBLICATIONS

D. H. Johnston et al.; Electrochemical Measurement of the Solvent Accessbility of Nucleobases Using Electron Transfer between DNA and Metal Complexes, *J. Am. Chem. Soc.* 117:8933–8938 (1995).
K. M. Millan et al.; Sequence–Selective Biosensor for DNA Based on Electroactive Hybridization Indicators, *Anal. Chem.* 65:2317–2323 (1983).
W. Bains; The Chip of the 90s, *Chem. in Britain* 122–125 (Feb. 1995).
T. J. Meade et al.; Electron Transfer through DNA: Site–Specific Modification of Duplex DNA with Ruthenium Donors and Acceptors, *Angew. Chem. Int. Ed. Engl.* 34 No. 3:352–354 (1995).
S. P. A. Fodor et al.; Multiplexed biochemical assays with biological chips, *Product Review* 364:555–556 (1993).
S.P.A. Fodor et al.; Light–Directed, Spatially Addressable Parallel Chemical Synthesis, *Science* 251:767–773 (1991).
Z. Du et al.; Automated Fluorescent DNA Sequencing of Polymerase Chain Reaction Products, *Methods in Enzymology* 218:104–121 (1993).

(List continued on next page.)

*Primary Examiner*—W. Gary Jones
*Assistant Examiner*—Arun Chakrabarti
(74) *Attorney, Agent, or Firm*—Myers Bigel Sibley & Sajovec

(57) ABSTRACT

A method of detecting a nucleic acid (e.g., DNA, RNA) that contains at least one preselected base (e.g., adenine, guanine, 6-mercaptoguanine, 8-oxo-guanine, and 8-oxo-adenine) comprises (a) reacting the nucleic acid with a transition metal complex capable of oxidizing the preselected base in an oxidation-reduction reaction; (b) detecting the oxidation-reduction reaction; and (c) determining the presence or absence of the nucleic acid from the detected oxidation-reduction reaction at the preselected base. The method may be used in a variety of applications, including DNA sequencing, diagnostic assays, and quantitative analysis.

90 Claims, 11 Drawing Sheets

OTHER PUBLICATIONS

J. M. Hall et al.; An Electrochemical Method for Detection of Nucleic Acid Hybridisation, *Biochem. and Molecular Bio. Int'l.* 32: No. 1, 21–28 (1994).

D. Noble; DNA Sequencing on a Chip, *Anal. Chem.* 67, No. 5:201–204 (1995).

Y. Jenkins et al.; A Sequence–Specific Molecular Light Switch: Tetherin of an Oligonucleotide to a Dipyridophenazine Complex of Ruthenium(II), *J. Am. Chem. Soc.* 114:8736–8738 (1992).

K. M. Millan et al.; Voltammetric DNA Biosensor for Cystic Fibrosis Based on a Modified Carbon Paste Electrode, *Anal. Chem.* 66:2943–2948 (1994).

M. T. Carter et al.; Voltammetric Studies of the Interaction of Metal Chelates with DNA. 2. Tris–Chelated Complexes of Colbalt(III) and Iron(II) with 1,10–Phenanthroline and 2,2'–Bipyridine, *J. Am. Chem. Soc.* 111:8901–8911 (1989).

S. A. Strobel et al.; Minor Groove Recognition of the Conserved G□U Pair at the Tetrahymena Ribozyme Reaction Site, *Science* 267:675–679 (1995).

T. Reid et al.; Simultaneous visualization of seven different DNA probes by in situ hybridization using combinatorial fluorescence and digital imaging microscopy, *Proc. Natl. Acad. Sci. USA* 89:1388–1392 (1992).

R. Tizard et al.; Imaging of DNA sequences with chemiluminescence, *Proc. Natl. Acad. Sci. USA* 87:4514–4518 (1990).

A. Lishanski et al.; Mutation detection by mismatch binding protein, MutS, in amplified DNA: Application to the cystic fibrosis gene, *Proc. Natl. Acad. Sci. USA* 91:2674–2678 (1994).

C. J. Murphy et al; Fast photoinduced electron transfer through DNA intercalation, *Proc. Natl. Acad. Sci. USA* 91:5315–5319 (1994).

S. A. Strobel et al; Site–Specific Cleavage of a Yeast Chromosome by Oligonucleotide–Directed Triple–Helix Formation, *Science* 249:73–75 (1990).

C. J. Murphy et al; Long–Range Photoinduced Electron Transfer Through a DNA Helix, *Science* 262:1025–1029 (1993).

D. H. Johnston et al; Trans–Dioxorhenium(V)–Mediated Electrocatalytic Oxidation of DNA at Indium Tin–Oxide Electrodes: Voltammetric Detection of DNA Cleavage in Solution, *Imorg. Chem.* 33: 6388–6390 (1994).

M. Maeder et al; Nonlinear Least–Squares Fitting of Multivariate Absorption Data, *Anal. Chem.* 62: 2220–2224 (1990).

M. Rudolph et al; A Simulator for Cyclic Voltammetric Responses, *Analytical Chemistry* 66:589–600 (1994).

J. Osterryoung; Voltammetry for the Future, *Acc. Chem. Res.* 26 No. 3: 77–83 (1993).

M. A. Tracy et al; Dynamics of Rigid and Semirigid Rodlike Polymers, *Annu. Rev. Phys. Chem.* 43: 525–527 (1992).

A. M. Pyle et al; Mixed–Ligand Complexes of Ruthenium(II): Factors Governing Binding to DNA, *J. Am. Chem. Soc.* 111:3051–3058 (1989).

O. S. Fedorova et al, Application of Tris (2,2'–bipyridyl) ruthenium(III) for the Investigation of DNA Spatial Structure by a Chemical Modification Method, *Journal of Inorganic Biochemistry* 34:149–155 (1988).

S. Satyanarayana, et al; Neither Δ– nor Λ–Tris(phenanthroline)ruthenium(II) Binds to DNA by Classical Intercalation; *Biochemistry* 31 No. 39:9319–9324 (1992).

J. A. Saleeba et al; [19]Chemical Cleavage of Mismatch of Detect Mutations, *Methods in Enzymology* 217: 286–295 (1993).

S. Steeken et al; One–Electron–Reduction Potentials of Pyrimidine Bases, Nucleosides, and Nucleotides in Aqueous Solution. Consequences for DNA Redox Chemistry, *J. Am. Chem. Soc.* 114: 4701–4709 (1992).

K.R. Khrapko et al; Hybridization of DNA with oligonucleotides immobolized in gel: convenient method for detection of single base changes, *Mol. Biol.* 25(3): 718 (1991).

L. J. Maher III; Inhibition of T7 RNA Polymerase Initiation by Triple–Helical DNA Complexes: A Model for Artificial Gene Repression, *Biochemistry* 31 No. 33; 7587–7594 (1992).

Adams et al.; editors The Biochemistry of Nucleic Acids, *Chapman & Hall, New York*, pp 519–524 (1992).

Evans, et al., a New Generation of DNA Chip Devices: Electronically Controlled DNA Hybridization on Semiconductors, *1995 AAAS Annual Meeting and Science Innovation Exposition: The 161st National Meeting of the American Association for the Advancement of Science* (Feb., 1995).

Millan, et al., Sequence–Selective Biosensor for DNA Based on Electroactive Hybridization Indicators, *Analytical Chemistry*, vol. 65, pp. 2317–2323 (Mar. 1993).

* cited by examiner

Mg²⁺
dGTP
TERMINAL TRANSFERASE

ELECTROCHEMICAL DETECTION OF NUCLEIC ACID HYBRIDIZATION

This application is a divisional of pending application Ser. No. 09/179,665, filed Oct. 27, 1998, now U.S. Pat. No. 6,132,971 which is in turn a divisional application of Ser. No. 08/667,338, filed Jun. 20, 1996, now issued as U.S. Pat. No. 5,871,918, which is in turn a continuation-in-part of and claims priority from application Ser. No. 08/495,817, filed Jun. 27, 1995 now ABN (converted to provisional application No. 60/060,949, filed Jun. 27, 1995), and which claims priority from provisional application No. 60/016,265, filed Apr. 19, 1996, the disclosures of all of which are incorporated by reference herein in their entirety.

This application is a continuation-in-part of copending application Ser. No. 08/495,817 filed Jun. 27, 1995, and is a continuation-in-part of copending application Serial No. 60/016,265 filed Apr. 19, 1996, the disclosures of which are incorporated by reference herein in their entirety.

FIELD OF THE INVENTION

The present invention relates to nucleic acid hybridization and sequencing, and particularly to methods of qualitatively and quantitatively detecting nucleic acid hybridization and to methods of nucleic acid sequencing.

BACKGROUND OF THE INVENTION

The detection of individual DNA sequences in heterogenous samples of DNA provides a basis for identifying genes, DNA profiling, and novel approaches to DNA sequencing. One approach to DNA hybridization detection involves the use of surface bound DNA sequences which can be assayed using an analytical response that indicates hybridization of the surface-bound oligomer to a sequence in the heterogeneous sample. These analytical methods generally involve laser-induced fluorescence arising from a covalently attached label on the target DNA strand, which is not sensitive to single-base mismatches in the surface-bound duplex. For example, U.S. Pat. Nos. 5,143,854 and 5,405,783 to Pirrung et al.; Fodor, et al., *Nature* 364:555 (1993); Bains, *Angew. Chem.* 107:356 (1995); and Noble, *Analytical Chemistry* 67(5):201A (1995) propose surfaces or "chips" for this application. In an alternate method, proposed by Hall, et al., *Biochem. and Molec. Bio. Inter.* 32(1):21 (1994), DNA hybridization is detected by an electrochemical method including observing the redox behavior of a single stranded DNA as compared to a double stranded DNA. This technique is also not sensitive to single-base mismatches in the DNA sample. Techniques for detecting single-base mismatches include enzymatic or chemical cleavage studies, such as those proposed in U.S. Pat. No. 5,194,372 to Nagai et al. However, these techniques are disadvantageous inasmuch as they require more time and separation technology.

U.S. Pat. No. 5,312,527 to Mikkelson et al. describes a voltammetric sequence-selective sensor for detecting target nucleic acid in which a double-stranded nucleic acid is contacted to a redox-active complex. The complex binds non-specifically to the double-stranded DNA. Because the complex itself is the redox-active compound that provides a voltammetric signal, the complex does not function in a catalytic manner without the addition of an enzyme.

U.S. Pat. No. 4,840,893 to Hill et al. describes an electrochemical assay for nucleic acids in which a competitive binding event between a ligand and an antiligand is in turn detected electrochemically.

Accordingly, there remains a need in the art for a method of detecting DNA hybridization, including a method of detecting single-base pair mismatches, which is both rapid and sensitive, and which can be rapidly applied on-line.

SUMMARY OF THE INVENTION

In general, the present invention provides a method of detecting a nucleic acid that contains at least one preselected base (e.g., adenine, guanine, 6-mercaptoguanine, 8-oxo-guanine, and 8-oxo-adenine). The method comprises (a) reacting the nucleic acid with a transition metal complex capable of oxidizing the preselected base in an oxidation-reduction reaction; (b) detecting the oxidation-reduction reaction; and (c) determining the presence or absence of the nucleic acid from the detected oxidation-reduction reaction at the preselected base. Depending on the particular embodiment of the method and the particular object desired, the method may optionally include the step of contacting the nucleic acid with a complementary nucleic acid to form a hybridized nucleic acid.

As a first aspect, the present invention provides a method of detecting DNA hybridization. The method includes (a) contacting a DNA sample with an oligonucleotide probe to form a hybridized DNA, (b) reacting the hybridized DNA with a transition metal complex capable of oxidizing a preselected base in the oligonucleotide probe in an oxidation-reduction reaction where the oligonucleotide probe has at least one of the preselected bases, (c) detecting the oxidation-reduction reaction, (d) determining the presence or absence of hybridized DNA from the detected oxidation-reduction reaction at the preselected base. As discussed in detail below, the step of detecting the oxidiation-reduction reaction may, in general, be carried out by measuring electron flow from the preselected base.

As a second aspect, the present invention provides another method of detecting DNA hybridization. The method includes (a) contacting a DNA sample with an oligonucleotide probe to form a hybridized DNA, (b) reacting the hybridized DNA with a transition metal complex capable of oxidizing a preselected base in the oligonucleotide probe in an oxidation-reduction reaction, where the oligonucleotide probe has at least one of the preselected bases, (c) detecting the oxidation-reduction reaction, (d) measuring the reaction rate of the detected oxidation-reduction reaction, (e) comparing the measured reaction rate to the oxidation-reduction reaction rate of the transition metal complex with a single-stranded DNA, and then (f) determining whether the measured reaction rate is essentially the same as the oxidation-reduction reaction rate of the transition metal complex with single-stranded DNA.

As a third aspect, the present invention provides an apparatus for detecting DNA hybridization. The apparatus includes (a) a plurality of DNA sample containers, (b) sample handling means for carrying the plurality of DNA sample containers, (c) an oligonucleotide probe delivery means for delivering the oligonucleotide probe to each of the DNA sample containers, (d) a transition metal complex delivery means for delivering the transition metal complex to each of the plurality of DNA sample containers, and (e) an oxidation-reduction reaction detector for detecting an oxidation-reduction reaction.

As a fourth aspect, the present invention provides a second apparatus for detecting DNA hybridization. The apparatus includes (a) a DNA sample container, (b) an oligonucleotide probe delivery means for delivering a plurality of oligonucleotide probes to the DNA sample container, (c) a transition metal complex delivery means for delivering the transition metal complex to the DNA sample container, and (d) an oxidation-reduction reaction detector for detecting an oxidation-reduction reaction.

As a fifth aspect, the present invention provides a method of sequencing DNA. The method includes (a) contacting a DNA sample with an oligonucleotide probe to form a hybridized DNA, where the oligonucleotide probe includes a preselected synthetic base having a unique oxidation potential, (b) reacting the hybridized DNA with a transition metal complex capable of oxidizing the preselected synthetic base in the oligonucleotide probe in an oxidation-reduction reaction, where the oligonucleotide probe has a predetermined number of the preselected synthetic bases, (c) detecting the oxidation-reduction reaction, (d) measuring the reaction rate of the detected oxidation-reduction reaction, and (e) identifying the base paired with the preselected synthetic base.

The foregoing and other aspects of the present invention are explained in detail in the detailed description set forth below.

BRIEF DESCRIPTION OF THE DRAWINGS

FIG. 12 shows the cyclic voltammograms of $Os(bpy)_3^{2+}$ (200 $\mu$M) using nylon-modified ITO electrodes soaked in buffer or in DNA.

DETAILED DESCRIPTION OF THE INVENTION

Figure 1:
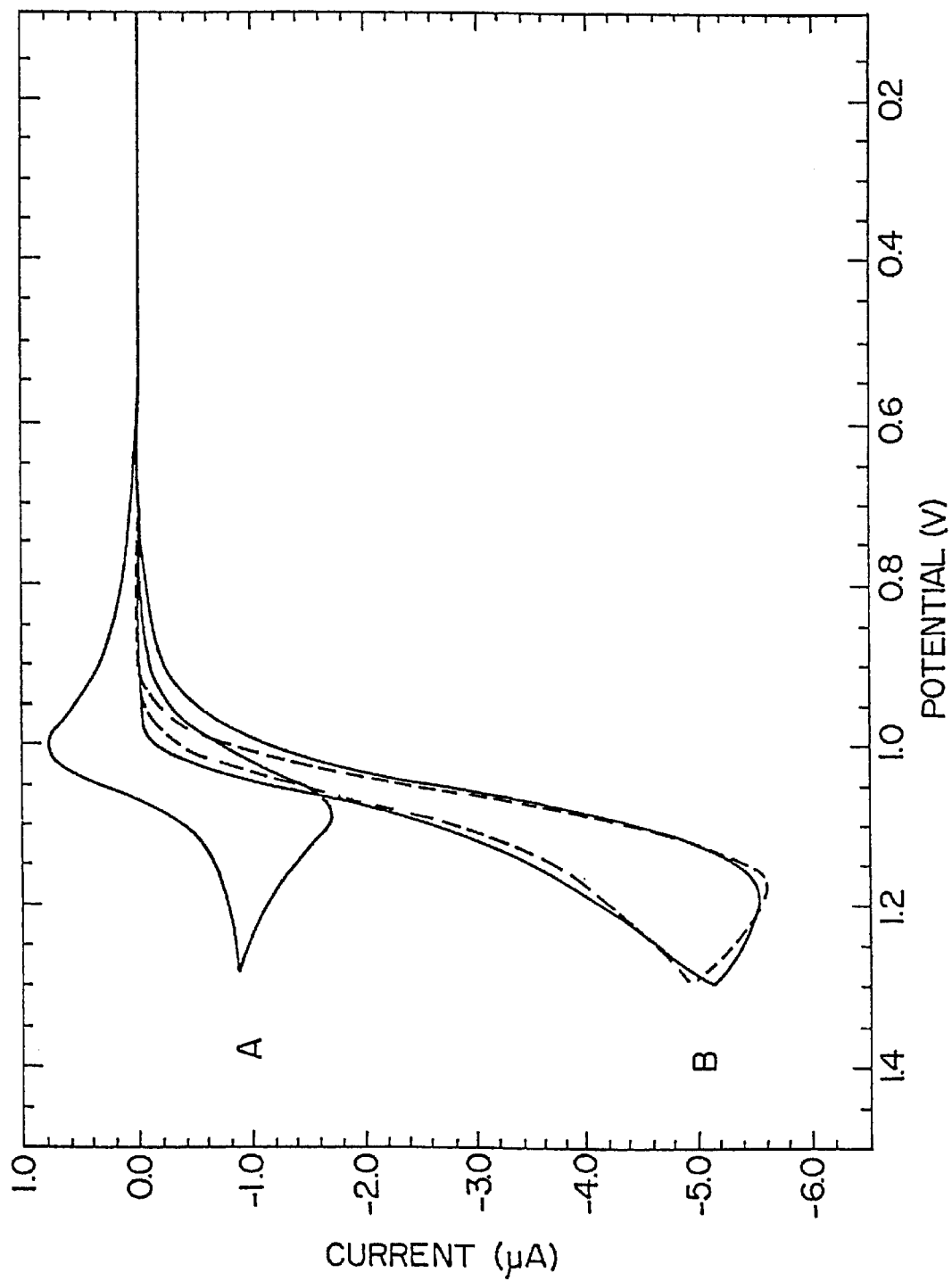
FIG. 1 shows the cyclic voltammograms of $Ru(bpy)_3^{2+}$ with and without calf thymus DNA. The solid line represents the scan of 50 $\mu$M $Ru(bpy)_3^{2+}$ at 25 mV/s in 700 mM NaCl/50 mM sodium phosphate buffer. The dotted line represents the voltammogram of 50 $\mu$M $Ru(bpy)_3^{2+}$ and 3.0 mM (nucleotide) calf thymus DNA.

The term "nucleic acid" as used herein refers to any nucleic acid, including both DNA and RNA. Nucleic acids of the present invention are typically polynucleic acids; that is, polymers of individual nucleotides that are covalently joined by 3', 5' phosphodiester bonds.

The term "complementary nucleic acid" as used herein refers to any nucleic acid, including oligonucleotide probes, that specifically binds to another nucleic acid to form a hybridized nucleic acid.

The phrase "determining the presence or absence of" is intended to include both qualitatively determining and quantitatively determining the presence or absence of the detected event (e.g., DNA hybridization, RNA hybridization, detecting target nucleic acid, etc.).

The terms "hybridized DNA" and "hybridized nucleic acid" refer to a single-stranded DNA which is hybridized to form a double-stranded DNA or nucleic acid, or a double-stranded DNA or nucleic acid which is hybridized to form triple helix DNA or nucleic acid.

While the methods and apparatus of the present invention are sometimes explained with respect to DNA herein, this is for purposes of clarity, and it is to be understood that the methods and apparatus of the instant invention may be applied to other nucleic acids such as RNA.

A. Nucleic Acid Amplification Methods

Inasmuch as the processes of the present invention involve contacting the DNA sample to an oligonucleotide probe to produce a hybridized DNA, it may be desirable for certain applications to amplify the DNA prior to contacting with the probe. Amplification of a selected, or target, nucleic acid sequence may be carried out by any suitable means. See generally D. Kwoh and T. Kwoh, *Am. Biotechnol. Lab.* 8, 14–25 (1990). Examples of suitable amplification techniques include, but are not limited to, polymerase chain reaction (including, for RNA amplification, reverse-transcriptase polymerase chain reaction), ligase chain reaction, strand displacement amplification, transcription-based amplification (see D. Kwoh et al., *Proc. Natl. Acad Sci. USA* 86, 1173–1177 (1989)), self-sustained sequence replication (or "3SR") (see J. Guatelli et al., Proc. Natl. Acad. Sci. USA 87, 1874–1878 (1990)), the Qβ replicase system (see P. Lizardi et al., *Biotechnology* 6, 1197–1202 (1988)), nucleic acid sequence-based amplification (or "NASBA") (see R. Lewis, *Genetic Engineering News* 12 (9), 1 (1992)), the repair chain reaction (or "RCR") (see R. Lewis, supra), and boomerang DNA amplification (or "BDA") (see R. Lewis, supra). The bases incorporated into the amplification product may be natural or modified bases (modified before or after amplification), and the bases may be selected to optimize subsequent electrochemical detection steps.

Polymerase chain reaction (PCR) may also be carried out in accordance with known techniques. See, e.g., U.S. Pat. Nos. 4,683,195; 4,683,202; 4,800,159; and 4,965,188 (the disclosure of all U.S. Patent references cited herein are to be incorporated herein by reference). In general, PCR involves, first, treating a nucleic acid sample (e.g. ,in the presence of a heat stable DNA polymerase) with one oligonucleotide primer for each strand of the specific sequence to be detected under hybridizing conditions so that an extension product of each primer is synthesized which is complementary to each nucleic acid strand, with the primers sufficiently complementary to each strand of the specific sequence to hybridize therewith so that the extension product synthesized from each primer, when it is separated from its complement, can serve as a template for synthesis of the extension product of the other primer, and then treating the sample under denaturing conditions to separate the primer extension products from their templates if the sequence or sequences to be detected are present. These steps are cyclically repeated until the desired degree of amplification is obtained. Detection of the amplified sequence may be carried out by adding to the reaction product an oligonucleotide probe capable of hybridizing to the reaction product (e.g., an oligonucleotide probe of the present invention), the probe carrying a detectable label, and then detecting the label in accordance with known techniques. Where the nucleic acid to be amplified is RNA, amplification may be carried out by initial conversion to DNA by reverse transcriptase in accordance with known techniques.

Strand displacement amplification (SDA) may be carried out in accordance with known techniques. See generally G. Walker et al., *Proc. Natl. Acad. Sci. USA* 89, 392–396 (1992); G. Walker et al., *Nucleic Acids Res.* 20, 1691–1696 (1992). For example, SDA may be carried out with a single amplification primer or a pair of amplification primers, with exponential amplification being achieved with the latter. In general, SDA amplification primers comprise, in the 5' to 3' direction, a flanking sequence (the DNA sequence of which is noncritical), a restriction site for the restriction enzyme employed in the reaction, and an oligonucleotide sequence (e.g., an oligonucleotide probe of the present invention) which hybridizes to the target sequence to be amplified and/or detected. The flanking sequence, which serves to facilitate binding of the restriction enzyme to the recognition site and provides a DNA polymerase priming site after the restriction site has been nicked, is preferably about 15 to 20 nucleotides in length; the restriction site is functional in the SDA reaction (i.e., phosphorothioate linkages incorporated into the primer strand do not inhibit subsequent nicking—a condition which may he satisfied through use of a nonpalindromic recognition site); the oligonucleotide probe portion is preferably about 13 to 15 nucleotides in length.

Ligase chain reaction (LCR) is also carried out in accordance with known techniques. See, e.g., R. Weiss, *Science* 254, 1292 (1991). In general, the reaction is carried out with two pairs of oligonucleotide probes: one pair binds to one strand of the sequence to be detected; the other pair binds to the other strand of the sequence to be detected. Each pair together completely overlaps the strand to which it corresponds. The reaction is carried out by, first, denaturing (e.g., separating) the strands of the sequence to be detected, then reacting the strands with the two pairs of oligonucleotide probes in the presence of a heat stable ligase so that each pair of oligonucleotide probes is ligated together, then separating the reaction product, and then cyclically repeating the process until the sequence has been amplified to the desired degree. Detection may then be carried out in like manner as described above with respect to PCR.

B. Oligonucleotide Probes

As noted above, the processes of the present invention are useful for detecting the hybridization of DNA. The first step of the process involves contacting a DNA sample with an oligonucleotide probe to form a hybridized DNA. The oligonucleotide probes which are useful in the methods of the present invention can be any probe comprised of between about 4 or 6 bases up to about 80 or 100 bases or more, more preferably between about 8 and about 15 bases. Oligonucleotide probes may be prepared having any of a wide variety of base sequences according to techniques which are well known in the art. Suitable bases for preparing the oligonucleotide probe may be selected from naturally occurring nucleotide bases such as adenine, cytosine, guanine, uracil, and thymine; and non-naturally occurring or "synthetic" nucleotide bases such as 7deaza-guanine 8-oxo-guanine, 6-mercaptoguanine, 4-acetylcytidine, 5-(carboxyhydroxyethyl)uridine, 2'-O-methylcytidine, 5-carboxymethylamino-methyl-2-thioridine, 5-carboxymethylaminomethyluridine, dihydrouridine, 2'-O- methylpseudouridine, β,D-galactosylqueosine, 2'-O-methylguanosine, inosine, N6-isopentenyladenosine, 1-methyladenosine, 1-methylpseeudouridine, 1-methylguanosine, 1-methylinosine, 2,2-dimethylguanosine, 2-methyladenosine, 2-methylguanosine, 3-methylcytidine, 5-methylcytidine, N6-methyladenosine, 7-methylguanosine, 5-methylamninomethyluridine, 5-methoxyaminomethyl-2-thiouridine, β,D-mannosylqueosine, 5-methloxycarbonylmethyluridine, 5-methoxyuridine, 2-methyltio-N6-isopentenyladenosine ,N-((9-β-D-ribofuranosyl-2-methylthiopurine-6-yl)carbamoyl)threonine, N-((9-β-D-ribofuranosylpurine-6-yl)N-methyl-carbamoyl)threonine, uridine-5-oxyacetic acid methylester, uridine-5-oxyacetic acid, wybutoxosine, pseudouridine, queosine, 2-thiocytidine, 5-methyl-2-thiouridine, 2-thiouridine, 2-thiouridine, 5-Methylurdine, N-((9-β-D-ribofuranosylpurine-6-yl)carbamoyl)threonine,2'-O-methyl-5-methyluridine,2'-O-methyluridine, wybutosine, and 3-(3-amino-3-carboxypropyl)uridine. Any oligonucleotide backbone may be employed, including DNA, RNA (although RNA is less preferred than DNA), modified sugars such as carbocycles, and sugars containing 2' substitutions such as fluoro and methoxy. The oligonucleotides may be oligonucleotides wherein at least one, or all, of the internucleotide bridging phosphate residues are modified phosphates, such as methyl phosphonates, methyl phosphonotlioates, phosphoroinorpholidates, phosphoropiperazidates and phosplioramidates (for example, every other one of the internucleotide bridging phosphate residues may be modified as described). The oligonucleotide may be a "peptide nucleic acid" such as described in P. Nielsen et al., Science 254, 1497–1500 (1991). The only requirement is that the oligonucleotide probe should possess a sequence at least a portion of which is capable of binding to a known portion of the sequence of the DNA sample. It may be desirable in some applications to contact the DNA sample with a number of oligonucleotide probes having different base sequences (e.g., where there are two or more target nucleic acids in the sample, or where a single target nucleic acid is hybridized to two or more probes in a "sandwich" assay).

C. Hybridization Methodology

The DNA (or nucleic acid) sample may be contacted with the oligonucleotide probe in any suitable manner known to those skilled in the art. For example, the DNA sample may be solubilized in solution, and contacted with the oligonucleotide probe by solubilizing the oligonucleotide probe in solution with the DNA sample under conditions which permit hybridization. Suitable conditions are well known to those skilled in the art (See, e.g., U.S. Pat. No. 4,358,535 to Falkow et al. and other U.S. Patent references citing the same) and include high salt concentration conditions. Alternatively, the DNA sample may be solubilized in solution with the oligonucleotide probe immobilized on a solid support, whereby the DNA sample may be contacted with the oligonucleotide probe by immersing the solid support having the oligonucleotide probe immobilized thereon in the solution containing the DNA sample.

D. Oxidizing Agents and Oxidation-Reduction Reactions

When a hybridization step precedes the oxidizing step, then after hybridization the hybridized DNA (or nucleic acid) is then reacted with a suitable oxidizing agent which is capable of oxidizing a preselected base in the oligonucleotide probe in an oxidation-reduction reaction. The preselected base can be any naturally occurring or synthetic nucleotide base in the oligonucleotide probe which undergoes oxidation upon reaction with the selected oxidizing agent. The preselected base exhibits a unique oxidation rate when paired as compared to when the preselected base is unpaired. The preselected base should exhibit unique oxidation rates when paired with each of the four naturally occurring bases. Generally, bases whose 5'-mononucleotides (e.g., the 5'-deoxyribonucleotide or 5'-ribonucleotide) exhibit rate constants above $10^4 M^{-1} s^{-1}$ can be detected using the catalytic reaction. Examples of suitable preselected bases include but are not limited to guanine, adenine, 8-oxo-guanine, and 8-oxo-adenine, 8-bromo-guanine, guanosine, xanthosine, wyosine, pseudouridine, 6-mercaptoguanine, 8-mercaptoguanine, 2-thioxanthine, 6-thioxanthine, 6-mercaptopurine, 2-amino-6-carboxymethyl-mercaptopurine, 2-mercaptopurine, 6-methoxypurine, 2-acetylamino-6-hydroxypurine, 6-methylthio-2-hydroxypurine, 2-dimethylamino-6-hydroxypurine, 2-hydroxypurine, 2-aminopurine, 6-amino-2-dimethylallyl-purine, 2-thioadenine, 8-hydroxyadenine, 8-methoxyadenine. Typically, the preselected base is selected from the group consisting of guanine, adenine, 6-mercaptoguanine, 8-oxo-guanine, and 8-oxo-adenine, with guanine being the currently preferred naturally occurring preselected base and 6-mercaptoguanine the currently preferred synthetic preselected base.

The oxidizing agent may be any charged molecule such as a cationic, anionic, or zwitterionic molecule which is reactive with the preselected base at a unique oxidation potential. Thus the selection of oxidizing agent will be dependent upon the particular preselected base chosen, and will be readily determinable by those skilled in the art. Particularly preferred oxidizing agents include transition metal complexes which are capable of metal-DNA electron transfer with the preselected base such that the reduced form of the metal complex is regenerated, completing a catalytic cycle. Examples of suitable transition metal complexes for use in the methods of the present invention include, for example, $Ruthenium^{2+}$ $(2,2'$-bipyridine$)_3$ ("Ru(bpy)$_3^{2+}$"), $Ruthenium^{2+}$ (4,4'-dimethyl-2,2'-bipyridine)$_3$("Ru(Me$_2$-bpy)$_3^{2+}$"), $Ruthenium^{2+}$(5,6-dimethyl-1,10-phenanthroline)$_3$ ("Ru(Me$_2$-phen)$_3^{2+}$"), $Iron^{2+}$(2,2-bipyridine)$_3$ ("Fe(bpy)$_3^{2+}$"), $Iron^{2+}$(5-chlorophenanthroline)$_3$ ("Fe(5-Cl-phen)$_3^{2+}$"), $Osmium^{2+}$ (2,2'-bipyridine)$_3$ ("Os(bpy)$_3^{2+}$"), $Osmium^{2+}$(5-chlorophenanthroline)$_3$ ("Os(5-Cl-phen)$_3^{2+}$"), $dioxorhenium^{1+}$phosphine, and $dioxorhenium^{1+}$pyridine ("ReO$_2$(py)$_4^{1+}$"). Some anionic complexes useful as oxidizing agents are: Ru(bpy)((SO$_3$)$_2$-bpy)$_2^{2-}$ and Ru(bpy)((CO$_2$)$_2$-bpy)$_2^{2-}$ and some zwitterionic complexes useful as oxidizing agents are Ru(bpy)$_2$((SO)$_2$-bpy) and Ru(bpy)$_2$((CO$_2$)$_2$-bpy) where (SO$_3$)$_2$-bpy$^2$ is 4,4'-disulfonato-2,2'-bipyridine and (CO$_2$)$_2$-bpy$^{2-}$ is 4,4'-dicarboxy-2,2'-bipyridine. Suitable substituted derivatives of the pyridine, bypyridine and phenanthroline groups may also be employed in complexes with any of the foregoing metals. Suitable substituted derivatives include but are not limited to 4-aminopyridine, 4-dimethylpyridine, 4-acetylpyridine, 4-nitropyridine, 4,4'-diamino-2,2'-bipyridine, 5,5'-diamino-2,2'-bipyridine, 6,6'-diamino-2,2'-bipyridine, 4,4'-diethylenediamine-2,2'-bipyridine, 5,5'-dietliylenediamine-2,2'-bipyridine, 6,6'-diethylenediamine-2,2'-bipyridine, 4,4'-dihydroxyl-2,2'-bipyridine, 5,5'-dihydroxyl-2,2'-bipyridine, 6,6'-dihydroxyl-2,2'-bipyridine, 4,4',4"-triamino-2,2',2"-terpyridine, 4,4',4"-triethylenediamine-2,2',2"-terpyridine, 4,4',4"-trihydroxy-2, 2',2"-terpyridine, 4,4',4"-trinitro-2,2',2"-terpyridine, 4,4',4"-triphenyl-2,2',2"-terpyridine, 4,7-diamino-1,10-phenanthroline, 3,8-diamino-1,10-phenanthroline, 4,7- diethylenediamine-1,10-phenanthroline, 3,8-diethylenediamine-1,10-phenanthroline, 4,7-dihydroxyl-1,10-phenanthroline, 3,8-dihydroxyl-1,10-phenanthroline, 4,7-dinitro-1,10-phenanthroline, 3,8-dinitro-1,10-phenanthroline, 4,7-diphenyl-1,10-phenanthroline, 3,8-diphenyl-1,10-phenanthroline, 4,7-disperamine-1,10-phenanthroline, 3,8-disperamine-1,10-phenanthroline, and dipyrido[3,2-a:2',2'-c]phenazine.

The oxidizing agent may be reacted with the hybridized DNA according to any suitable technique, to effect the oxidation-reduction reaction of the oxidizing agent with the preselected base. All that is required is that the oxidizing agent be reacted with the hybridized DNA sample under conditions sufficient to effect the selective oxidation of the preselected base. For example, the transition metal may be reacted with solubilized hybridized DNA by solubilizing the oxidizing agent in the solution containing the solubilized hybridized DNA under conditions sufficient to permit the oxidation-reduction reaction between the oxidizing agent and the preselected base to occur. Alternatively, in the embodiment wherein the hybridized DNA is immobilized on a solid support, the oxidizing agent may be reacted with the hybridized DNA by immobilizing the oxidizing agent on the same solid support and immersing the solid support in a solution under conditions sufficient to permit the oxidation-reduction reaction of the oxidizing agent and the preselected base to occur. The solvent in which the oxidation-reduction reaction takes place may be any suitable solvent for solubilizing DNA, and preferably comprises water. Suitable conditions for permitting the oxidation-reduction reaction to occur will be known to those skilled in the art.

In a hybridized DNA or nucleic acid, the oxidizing agents Dock in the minor groove of DNA, thus intimate contact between the preselected base and the oxidizing agent is precluded by the unique structure of the double (or triple) helix. This protection of the preselected base residue results in the necessity of electron tunneling through solvent, which attenuates the rate of electron transfer. The solvent accessibility varies with the nature of the nucleotide base which is paired with the preselected base. The tunneling distance can be estimated according to the formula:

$$k/k_{ss} = \exp(-\beta \Delta r)$$

where $\Delta r$ is the change in distance in the duplex compared to the single strand and $k_{ss}$ is the rate constant for oxidation of the preselected base in the single-stranded DNA sample. Thus, the tunneling distance between the preselected base and the oxidizing agent is different for each base pairing and for unpaired DNA. Therefore, the electron-transfer rate constant indicates the identity of the paired (or mismatched) base. If the driving force for electron transfer is significantly less than the reorganizational energy ($\lambda$), a plot of RT ln k against driving force, corrected for work terms associated with the approach of the reactants, yields a straight line with a slope of ½, according to Marcus theory. Based on Marcus theory then, the absolute rate constants can be calculated by the following equation:

$$k = \nu \exp[-\beta(r-r_0)]\exp[-(\Delta G+\lambda)^2/4\lambda RT]$$

wherein $\nu$ is the rate constant in the diffusion-controlled limit ($10^{11}$ $M^{-1}s^{-1}$), r is the distance between the reactant and product in the activated complex, $r_0$ is the distance of closest approach of reactant and product, and $\beta$ is the influence of the intervening medium. Because, as noted above, the preselected base is incorporated into the interior of the hybridized DNA, this imposes a finite distance across which the electron must tunnel to the oxidizing agent. Thus, r does not equal $r_0$. $\beta$ for water is about 3 $Å^{-1}$. This relatively large value for $\beta$ indicates that significant changes in the electron-transfer rate constants will be effected by very small changes in the tunneling distance. Since the DNA conformation between the preselected base and the base paired with the preselected base is dependent upon the base paired with the preselected base, the base paired with the preselected base affects the tunneling distance through which the electron must tunnel between the preselected base and the oxidizing agent. A correlation between the Tunneling distance and the specific base paired with the preselected base is therefore established.

E. Detection of Oxidation-Reduction Reactions

The occurrence of the oxidation-reduction reaction may be detected according to any suitable means known to those skilled in the art. For example, the occurrence of the oxidation-reduction reaction may be detected using a detection electrode to observe a change in the electronic signal which is indicative of the occurrence of the oxidation-reduction reaction. Typically, a detection electrode which is sensitive to the transfer of electrons between the oxidizing agent and the hybridized DNA is placed in contact with the solution containing the reacted hybridized DNA and oxidizing agent. Generally, a reference electrode and an auxiliary electrode are also placed in contact with the solution in conjunction with the detection electrode (with most of the current passing through the auxiliary electrode). Suitable detection electrodes will be well known to those skilled in the art and include, for example, a glassy carbon electrode or an indium tin oxide electrode. Similarly, suitable reference electrodes will also be known in the art and include, for example, silver/silver chloride electrodes.

The detection of the electronic signal associated with the oxidation-reduction reaction permits the determination of the presence or absence of hybridized DNA. The step of determining the presence or absence of hybridized DNA typically includes (i) measuring the reaction rate of the oxidation-reduction reaction, (ii) comparing the measured reaction rate to the oxidation-reduction reaction rate of the transition metal complex with a single-stranded DNA, and then (iii) determining whether the measured reaction rate is essentially the same as the oxidation-reduction reaction rate of the transition metal complex with single-stranded DNA. The step of measuring the reaction rate may be carried out by any suitable means. For example, the relative reaction rate may be determined by comparing the current as a function of scan rate, probe concentration, target concentration, mediator, buffer, temperature, and/or electrochemical method.

The oxidation-reduction reaction rate may be measured according to suitable means known to those skilled in the art. Typically, the oxidation-reduction reaction rate is measured by measuring the electronic signal associated with the occurrence of the oxidation-reduction reaction. For example, the electronic signal associated with the oxidation-reduction reaction may be measured by providing a suitable apparatus in electronic communication with the detection electrode. A suitable apparatus will be capable of measuring the electronic signal which is generated so as to provide a measurement of the oxidation-reduction reaction rate of the reaction of the hybridized DNA and the oxidizing agent. The electronic signal may be characteristic of any electrochemical method, including cyclic voltammetry, normal pulse voltammetry, chronoamperometry, and square-wave voltammetry, with cyclic voltammetry being the currently preferred form.

The measured reaction rate may then be compared to the known oxidation-reduction reaction rate of the transition metal complex with a single-stranded DNA. As discussed in detail above, the tunneling distance between the oxidizing agent and the selected base in either the hybridized or single-stranded DNA affects the oxidation-reduction reaction rate of the reaction between the oxidizing agent and the preselected base. Accordingly, hybridized DNA exhibits a different oxidation-reduction reaction rate than single-stranded DNA. The presence or absence of hybridized DNA at the preselected base can be determined by determining whether or not the measured oxidation-reduction reaction rate is the same as the oxidation-reduction reaction rate of the oxidizing agent and the preselected base in single-stranded DNA. Furthermore, the tunneling distance between the oxidizing agent and the preselected base will differ according to the bond distance between the preselected base and its pair, such that each possible base pairing may be distinguished from the others. The bond distance between the preselected base and its base pair is dependent upon the base which is paired with the preselected base. For example, the oxidation-reduction reaction rate for the oxidation of guanine paired with adenine differs from the oxidation-reduction reaction rate for the oxidation of guanine paired with cytosine, which in turn is different from the oxidational-reduction reaction rate for tIle oxidation of guanine paired with guanine, which is also different from the oxidation-reduction reaction rate for the oxidation of guanine paired with thymine. More specifically, the oxidation-reduction reaction rates for the oxidation of guanine follow the trend wherein single strand guanine is greater than guanine paired with adenine, which is greater than guanine paired with guanine, which is greater than guanine paired with thymine, which is greater than guanine paired with cytosine. Accordingly, the methods of the present invention are useful for detecting single-base pair mismatches at the preselected base or at the base pair adjacent to the preselected base.

Advantageously, the distinction between the oxidation-reduction reaction rates of the oxidation of the preselected base when paired with each of the various naturally occurring bases also permits the identification of the base paired with the preselected base. The base paired with the preselected base may be identified by (i) measuring the reaction rate of the detected oxidation-reduction reaction, (ii) comparing the measured reaction rate to each of the four different known oxidation-reduction reaction rates of the oxidizing agent with a DNA having adenine, cytosine, guanine, or thymine bound to the preselected base, and (iii) determining which of the known oxidation-reduction reaction rates is essentially the same as the measured reaction rate. The reaction rate may be measured according to techniques described above. Similarly, the reaction rates of each of the four different oxidation-reduction reactions of the oxidizing agent with a DNA having adenine, cytosine, guanine or thymine bound to the preselected base may be measured according to the same techniques such that these reaction rates are known. The measured reaction rate of the oxidation-reduction reaction of the oxidizing agent with the hybridized DNA may then be compared to the known oxidation-reduction reaction rates of the oxidizing agent with a DNA having adenine, cytosine, guanine or thymine bound to the preselected base. For example, the base paired with the preselected base is determined by determining the known base pairing having the oxidation-reduction reaction rate which is essentially the same as the measured oxidation-reduction reaction rate.

F. DNA Sequencing

The present invention also provides a method of sequencing DNA comprising (a) contacting a DNA sample with an oligonucleotide probe to form a hybridized DNA, the oligonucleotide probe including a preselected synthetic base having a unique oxidation potential; (b) reacting the hybridized DNA with an oxidizing agent such as a transition metal complex, capable of oxidizing the preselected synthetic base in the oligonucleotide probe in an oxidation-reduction reaction, the oligonucleotide probe having a predetermined number of the preselected synthetic bases; (c) detecting the oxidation-reduction reaction; (d) measuring the reaction rate of the detected oxidation-reduction reaction; and (e) identifying the base paired with the preselected synthetic base.

As in the methods discussed hereinabove, the DNA sample may be amplified prior to the step of contacting with the oligonucleotide probe, according to techniques known to those skilled in the art. The synthetic base may be selected from the group of bases described hereinabove, and other synthetic bases known to those skilled in the art. The only limitation is that the synthetic base should possess a unique oxidation potential as compared with the oxidation potentials of the four naturally occurring bases, i.e., adenine, cytosine, guanine, and thymine. The steps of contacting the DNA sample with the oligonucleotide probe; reacting the hybridized DNA with the oxidizing agent, detecting the oxidation-reduction reaction, and measuring the reaction rate may be carried out as described hereinabove. The step of identifying the base paired with the preselected synthetic base includes the steps of (i) comparing the measured reaction rate to each of the four different known oxidation-reduction reaction rates of the oxidizing agent with the DNA having adenine, cytosine, guanine, or thymine bound to the preselected synthetic base; and (ii) determining which of the known oxidation-reduction reaction rates is essentially the same as the measured reaction rate.

In another embodiment, the oligonucleotide probe further includes a second preselected synthetic base. The second preselected synthetic base has a unique oxidation potential which is different from the oxidation potential of the first preselected synthetic base. In this embodiment, the step of detecting the oxidation-reduction reaction of the oxidizing agent with the preselected base further includes detecting the oxidation-reduction reaction of the oxidizing agent with the second preselected synthetic base as well. In addition, the step of measuring the oxidation-reduction reaction rate further includes measuring the oxidation-reduction reaction rate of the oxidation of the second preselected base by the oxidizing agent as well. Further, the step of identifying the base paired with the preselected synthetic base further includes identifying the base paired with the second preselected synthetic base as well. According to this embodiment, the oxidation-reduction reactions of both preselected bases may be detected such that ultimately the bases which are paired with each preselected synthetic base may be identified using the method described hereinabove. As will be apparent to those skilled in the art, the foregoing method may be carried out with more than two preselected synthetic bases, provided that each preselected synthetic base exhibits a unique oxidation potential which is different from the oxidation potential of all other preselected synthetic bases, and different from the oxidation potential of each of the four naturally occurring bases.

Inasmuch as each base which is paired with a preselected base may be identified according to the methods described herein, DNA may be sequenced by repeating the steps of the foregoing method with a sufficient number of different oligonucleotide probes having the preselected synthetic base at different sites to identify each base in the DNA sample. In other words, the DNA sample may be sequenced by providing a sufficient number of oligonucleotide probes wherein each probe sequence includes at least one of the preselected synthetic bases, and the synthetic base is located at a different and calculated site along the probe sequence in each oligonucleotide probe. In this manner, repeated detection of the oxidation-reduction reaction of the hybridized DNA with an oxidizing agent, measurement of the oxidation-reduction reaction rate, and identification of the base paired with the preselected synthetic base will result in a base-by-base identification of the sequence of the DNA sample.

G. Apparatus

Figure 3:
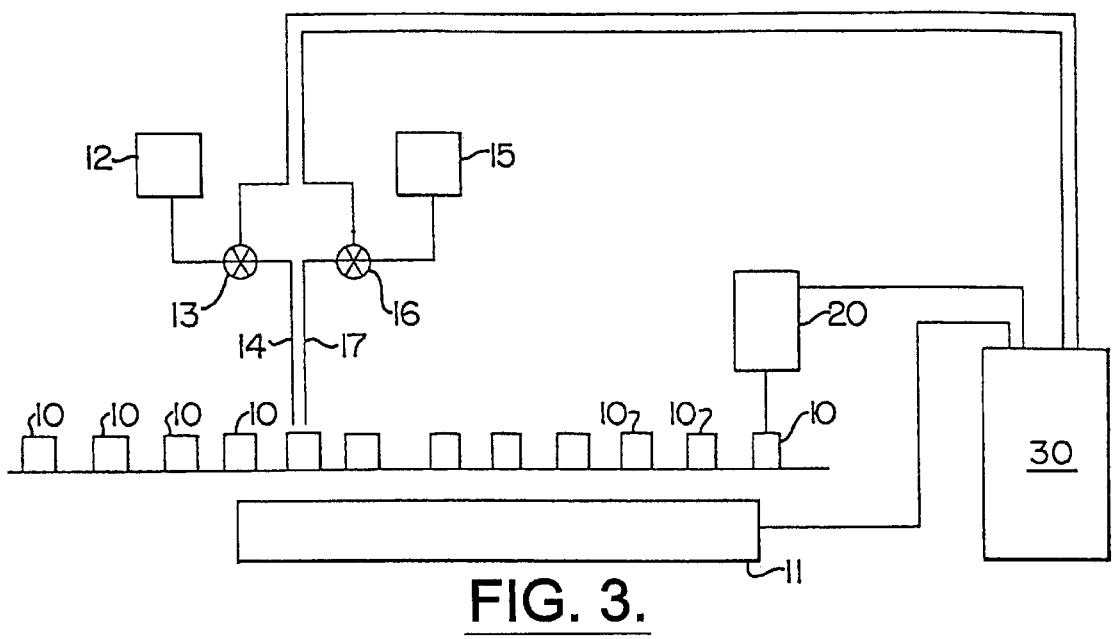
FIG. 3 is a schematic illustration of one illustrative apparatus useful for carrying out the methods of the present invention.

The present invention also provides apparatus useful for carrying out the methods of the present invention. One such illustrative apparatus is schematically illustrated in FIG. 3. In general, the apparatus comprises a plurality of DNA sample containers 10. A drive assembly 11 serves as a sample handling means for carrying the plurality of DNA sample containers. A liquid reservoir 12, a feed line 13 and a valve 14 serve as an oligonucleotide probe delivery means for delivering the oligonucleotide probe to each of the DNA sample containers, and a corresponding liquid reservoir 15, feed line 16 and valve 17 serves as an oxidizing agent delivery means for delivering the transition metal complex to each of the plurality of DNA sample containers. A probe assembly 20 including a drive 21 and a probe 22 serves as an oxidation-reduction reaction detector means for detecting an oxidation-reduction reaction. In operation, DNA samples are pre-deposited in the sample containers 10. The drive assembly 11 then transports consecutively the sample containers 10 beneath the oligonucleotide probe delivery means and the oxidizing agent delivery means for delivering the respective reagents therein. After reagent delivery, the respective sample container is advanced by the drive means to a position beneath the probe 22 and the probe 22 advanced by the drive 21 into the sample container for detection of the oxidation-reduction reaction. Additional electrodes necessary for carrying out of the cyclic voltamogram are carried with the probe 22. Operation of the various components and collection of data may be carried out with a suitable controller 30, such as a software program running on a general purpose computer.

Numerous variations on the foregoing apparatus will, of course, he readily apparent to those skilled in the art. The plurality of DNA sample containers may be any suitable container known to those skilled in the art, and includes microtiter plates, test tubes, petri dishes, culture vials, solid supports, and the like, which are capable of containing the DNA sample. The sample handling means may be any suitably designed sample container handling means known to those skilled in the art, which is capable of carrying the DNA sample containers.

Suitable oligonucleotide probe delivery means for delivering the oligonucleotide probe to each of the DNA sample containers are well known in the art. For example, according to one embodiment, the oligonucleotide probe delivery means comprises a solid support on which the oligonucleotide probe is immobilized. The oligonucleotide probe delivery means should permit sufficient contact between the DNA sample and the oligonucleotide probe under appropriate conditions to effect hybridization of the DNA sample and the oligonucleotide probe. Suitable oxidizing agent delivery means for delivering the oxidizing agent to each of the plurality of DNA sample containers are well known in the art. For example, according to one embodiment, the oxidizing agent is attached to a solid support which comprises the oxidizing agent delivery means. The oxidation-reduction reaction detector for detecting an oxidation-reduction reaction may, according to one embodiment, comprise one or more electrodes which are capable of detecting the oxidation of the preselected base. Suitable detection electrodes and reference electrodes are described hereinabove with reference to the methods of the present invention. Preferably, the electrodes are in electronic communication with a means for measuring the oxidation-reduction reaction rate of the oxidation-reduction reaction. Suitable means for measuring the oxidation-reduction reaction rate are known to those skilled in the art as described hereinabove.

In an alternate embodiment of the apparatus of the present invention, the apparatus for detecting DNA hybridization comprises (a) a DNA sample container; (b) an oligonucleotide probe delivery means for delivering a plurality of oligonucleotide probes to the DNA sample container; (c) an oxidizing agent delivery means for delivering the oxidizing agent to the DNA sample container; and (d) an oxidation-reduction reaction detector for detecting an oxidation-reduction reaction. This apparatus is adapted for use with immobilized probes such as those described in U.S. Pat. Nos. 5,143,854 and 5,405,783 to Pirrung et al.; Fodor, et al., *Nature* 364:555 (1993); Bains, *Agnew. Chem.* 107:356 (1995); and Noble, *Analytical Chemisty* 67(5):21 (1995), the disclosures of which are incorporated herein by reference in their entirety.

As noted above, the DNA sample container may be any suitable container known to those skilled in the art. The oligonucleotide probe delivery means is preferably a solid support having a plurality of oligonucleotide probes immobilized thereon, which is capable of delivering the probes to the DNA sample container. For example, according to one embodiment, the solid support having the plurality of oligonucleotide probes immobilized thereon is contacted with the DNA sample within the DNA sample container under conditions sufficient to permit the hybridization of the DNA sample with one or more oligonucleotide probes.

Suitable oxidizing agent delivery means for delivering the oxidizing agent to the DNA sample container are described hereinabove. The preferred oxidizing agent delivery means comprises a solid support having the oxidizing agent immobilized thereon. According to one preferred embodiment, the oxidizing agent and the plurality of oligonucleotide probes are immobilized on the same solid support.

The apparatus according to the present invention are useful for performing diagnostic assays of a variety of DNA samples. The plurality of oligonucleotide probes permits the assay and detection of a variety DNA within a single sample, thus providing a useful tool for the screening of a single sample for a variety of DNA including pathogens, viruses, and the like.

H. RNA Hybridization Detection, RNA Sequencing, and RNA Mismatch Detection

Also disclosed herein are methods of detecting RNA hybridization, RNA sequencing methods, and methods of detecting RNA mismatches. RNA useful for carrying out such methods, includes, but is not limited to, ribosomal RNA, transfer RNA, or genomic RNA (e.g., RNA obtained from RNA viruses such as retroviruses, HIV-1, etc.). A first aspect of the instant invention is, accordngly, a method of detecting RNA hybridization comprises: (a) contacting an RNA sample with an oligonucleotide probe to form a hybridized RNA; (b) reacting the hybridized RNA with a transition metal complex capable of oxidizing a preselected base in the oligonucleotide probe in an oxidation-reduction reaction, the oligonucleotide probe having at least one of the preselected bases; (c) detecting the oxidation-reduction reaction; (d) determining the presence or absence of hybridized RNA from the detected oxidation-reduction reaction at the preselected base.

More particularly, a method of detecting RNA hybridization comprises: (a) contacting an RNA sample with an oligonucleotide probe to form a hybridized RNA; (b) reacting the hybridized RNA with a transition metal complex capable of oxidizing a preselected base in the oligonucleotide probe in an oxidation-reduction reaction, the oligonucleotide probe having at least one of the preselected bases; (c) detecting the oxidation-reduction reaction; (d) measuring the reaction rate of the detected oxidation-reduction reaction; (e) comparing the measured reaction rate to the oxidation-reduction reaction rate of the transition metal complex with a single-stranded RNA; and then (f) determining whether the measured reaction rate is the same as the oxidation-reduction reaction rate of the transition metal complex with single-stranded RNA.

A method of sequencing RNA comprises: (a) contacting an RNA sample with an oligonucleotide probe to form a hybridized RNA, the oligonucleotide probe including a preselected base having a unique oxidation rate; (b) reacting the hybridized RNA with a transition metal complex capable of oxidizing the preselected base in the oligonucleotide probe in an oxidation-reduction reaction, the oligonucleotide probe having a predetermined number of the preselected bases; (c) detecting the oxidation-reduction reaction; (d) measuring the reaction rate of the detected oxidation-reduction reaction; and (e) identifying the base paired with the preselected base.

Oligonucleotide probes, hybridization methodology, oxidizing agents, detection of oxidation reduction reactions, and apparatus useful for carrying out these methods are essentially as given in sections A-H above, adapted for use with RNA as the nucleic acid sample in accordance with principles known to those skilled in the art (e.g., uracil replaces thymine as a base).

I. Detection of Preselected Base on Target Nucleic Acid

In the methods specifically described above, metal complexes are used to obtain an electrochemical current from single- and double-stranded DNA or nucleic acids. Preselected bases such as guanine give an electrochemical signal, and this signal is much weaker for double-stranded DNA. Such methods advantageously exhibit high structural sensitivity, and can resolve a single base mismatch. Such methods are therefore particularly advantageous for the sequencing of DNA. However, two drawbacks of such methods are that: (a) there is a negative signal on going from the probe strand to the hybrid, and (b) there is no amplification of the signal. The following techniques provide solutions to these problems. In addition, the following techniques are particularly useful for diagnostic assays, and are particularly useful for the the quantitative detection of nucleic acids.

In view of the foregoing, also disclosed herein is a method of detecting the presence or absence of a target nucleic acid in a test sample suspected of containing the same, wherein the target nucleic acid contains at least one preselected base. In contrast to the methods described above, in the instant method the preselected base is located on the target nucleic acid, rather than on the oligonucleotide probe.

The method may be carried out on a test sample containing the target nucleic acid. Any test sample suspected of containing the target nucleic acid may be used, including (but not limited to) tissue samples such as biopsy samples and biological fluids such as blood, sputum, urine, and semen samples, bacterial cultures, soil samples, food samples, etc. The target nucleic acid may be of any origin, including animal, plant or microbiological (e.g., viral, prokaryotic and eukaryotic bacterial, protozoal, fungal, protoctistal, etc.) depending on the particular purpose of the test. The sample may be processed or purified prior to carrying out the instant method in accordance with techniques known or apparent to those skilled in the art; and nucleic acids therein may be digested, fragmented, and/or amplified (see above) prior to carrying out the instant method, if so desired.

Figure 4:
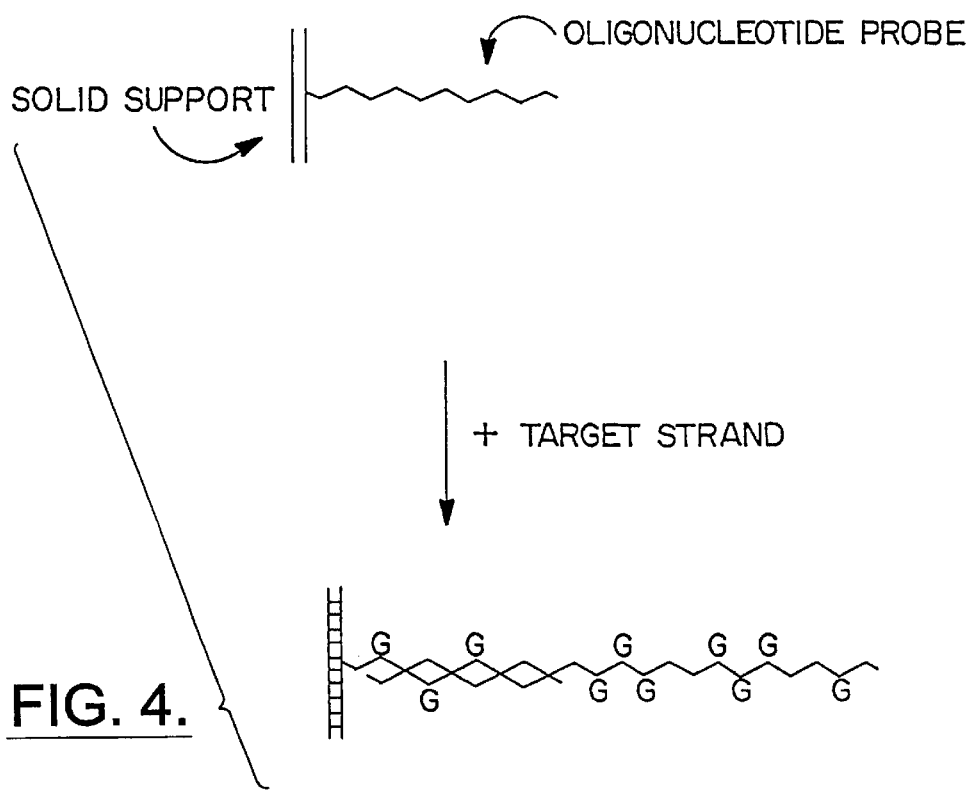
FIG. 4 is a schematic illustration of a detection method particularly advantageous for the quantitative detection of DNA where the preselected base is located on the target nucleic acid.

As schematically illustrated in FIG. 4, the method comprises (a) contacting the test sample to an oligonucleotide probe that specifically binds to the target nucleic acid to form a hybridized nucleic acid; (b) contacting the hybridized nucleic acid to a transition metal complex that oxidizes the preselected base in an oxidation-reduction reaction; (c) detecting the presence or absence of the oxidation-reduction reaction associated with the hybridized nucleic acid; and (d) determining the presence or absence of the target nucleic acid in the test sample from the detected oxidation-reduction reaction at the preselected base. As illustrated in FIG. 4, the oligonucleotide probe may be immobilized on a solid support to facilitate separating the test sample from the hybridized nucleic acid, with the separating step occuring prior to the detecting step (e.g., between steps (a) and (b) or between steps (b) and (c)). Alternatively, the oligonucleotide probe may be provided free in solution, and other means provided to separate the hybridized nucleic acid from the sample (e.g., by a mediator nucleic acid that binds to the oligonucleotide probe, or by a biotin-avidin binding interaction, where biotin is bound to the oligonucleotide probe and avidin is immobilized on a solid support).

Preferably, the target nucleic acid contains at least ten more of the preselected base than does the oligonucleotide probe, or more preferably at least 50 or 100 more of the preselected base than does the oligonucleotide probe. A larger current enhancement is advantageously obtained when the target nucleic acid contains many more of the preselected base than does the oligonucleotide probe.

Optionally, but preferably, the oligonucleotide probe is free of the preselected base, or is at least essentially free of the preselected base (i.e., contains sufficiently less of the preselected base that signal from probe does not interfere with or is not mistaken as a signal from the target nucleic acid). Where a sequence of naturally occuring bases is not available that will conveniently hybridize to the target nucleic acid, the strategy of employing alternate bases that are redox inactive (discussed below) may be employed.

The target nucleic acid is preferably longer than the oligonucleotide probe, and at least one of the preselected base is not hybridized to the oligonucleotide probe in the hybridized nucleic acid (i.e.., is an "overhanging" base), as illustrated in FIG. 4. Preferably, at least 10, 50, or 100 of the preselected bases are "overhanging" bases, thereby providing substantial amplification of the electrochemical signal detected.

For example, an oligonucleotide probe that does not contain any guanine residues (e.g., only A, T, and C) may be used. The cyclic voltammogram of Ru $(bpy)_3^{2+}$ in the presence of this strand is very similar to that without the oligomer. This strand is then hybridized to a target strand that contains guanines in either, or both (as illustrated in FIG. 4 by a "G" adjacent the target nucleic acid strand), the overlapping base-paired regions or in overhanging regions if the target nucleic acid is longer than the oligonucleotide probe. Because multiple guanines are detected, the signal is amplified relative to the number of hybrids formed. In a case where a genomic DNA or RNA is the target strand, large numbers (of overhanging guanines are encountered, which would give tremendous signal amplification. For example, ribosomal RNA may contain as many as 1,000 guanines for a particular organism, and would therefore provide approximately a 1,000-fold amplification per hybridization event.

For example, in one preferred embodiment, the assay for the preselected base on the target strand involves immobilization of the (preferably redox-silent) probe strand on a solid surface oriented close to the electrode surface, which provides a low background signal when scanned in the presence of the mediator. The solid surface is then contacted with a solution of the target strand, which contains the preselected base. If hybridization occurs, the target strand will now be in close proximity to the electrode, and a current enhancement will be detected.

Quantitating nucleic acids. The instant method is particularly well suited to the quantitative detection of nucleic acids. In the cases described in this section, the rate constant for oxidation of the hybrid by the oxidizing agent (e.g., $Ru(bpy)_3^{3+}$) can be determined from the cyclic voltammogram (or other electronic signal) by digital simulation. Under most conditions this reaction will obey second-order kinetics, so rate=$k[Ru(bpy)_3^{2+}]$ [DNA] where k is the rate constant that is specific for the particular probe-target hybrid, $[Ru(bpy)_3^{2+}]$ is the concentration of the oxidizing agent, and [DNA] is the concentration of the hybrid (which could be a DNA-RNA hybrid). If k and $[Ru(bpy)_3^{2+}]$ are known, then the quantity of the hybrid can be determined. In practice, a calibration curve for current enhancements obtained with different quantities of standard solutions containing target DNA or RNA is constructed and the current enhancement used to obtain the quantity of hybrid directly. This quantity is then related directly to the quantity of target material (e.g., infectious organism in a clinical sample). See, e.g., M. Holodniy et al., *J. Virol.* 69, 3510–3516 (1995); J. Mellors et al, *Science* 272, 1167–1170 (1996).

Oligonucleotide probes, hybridization methodology, oxidizing agents and oxidation-reduction reaction methods, detection of oxidation reduction reactions, and apparatus useful for carrying out these methods are as given in sections A–H above.

J. Alternate Bases that are Redox Inactive

One disadvantage to the method described in section H above is that the oligonucleotide probe preferably does not contain a substantial number of the preselected base (e.g., guanine). A solution to this problem is to use an alternate base that would substitute for guanine (i.e., a base that, like guanine, has a greater binding affinity for cytosine than do other bases in a nucleic acid duplex) in the probe strand but would not be oxidized by the oxidizing agent under the applicable reaction conditions. Examples of such alternate bases when guanine is the preselected base are inosine and 7-deaza-guanine.

Thus, a method of detecting a target nucleic acid, where the target nucleic acid contains at least one preselected base and the probe or capture nucleic acid contains alternate redox inactive bases comprises: (a) contacting the target nucleic acid to a complementary nucleic acid that specifically binds to the target nucleic acid to form a hybridized nucleic acid; (b) reacting the hybridized nucleic acid with a transition metal complex capable of oxidizing the preselected base in an oxidation-reduction reaction; (c) detecting the oxidation-reduction reaction; and (d) determining the presence or absence of the nucleic acid from the detected oxidation-reduction reaction at the preselected base. When the preselected base in the target nucleic acid is guanine and the target nucleic acid contains cytosine (which would originally bond with guanine in the complementary nucleic acid), then the complementary nucleic acid contains an alternate base that bonds to cytosine in the hybridized nucleic acid. The alternate base may be selected from the group consisting of inosine and 7-deaza-guanine. The reacting step typically comprises reacting the transition metal complex with the nucleic acid under conditions sufficient to effect the selective oxidation of the preselected base without oxidizing the alternate base.

Oligonucleotide probes, hybridization methodology, oxidizing agents and oxidation-reduction reaction methods, detection of oxidation reduction reactions, and apparatus useful for carrying out these methods are as given in sections A–I above.

K. Polymerization of Preselected Base with Terminal Transferase

Figure 7:
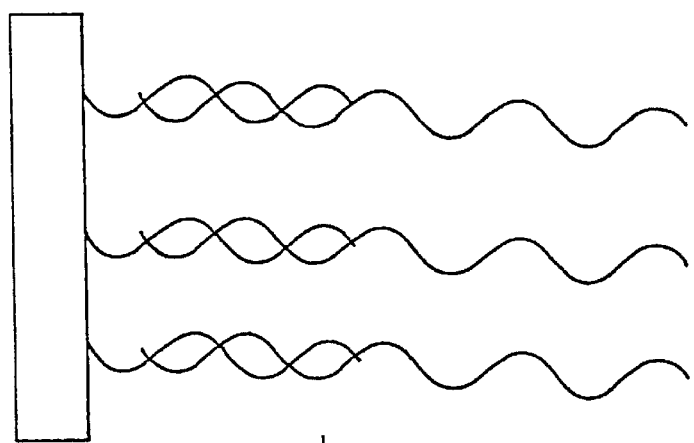
FIG. 7 schematically illustrates an alternate embodiment of the invention of FIG. 4, where the preselected bases are on an elongation product of terminal transferase.

An alternative embodiment of the method described in section H above involves elongating the target nucleic acid with terminal transferase to provide additional ones of the preselected base thereon. As illustrated in FIG. 7, such a method comprises: (a) contacting the test sample to an oligonucleotide probe that specifically binds to the target nucleic acid to form a hybridized nucleic acid, the oligonucleotide probe having end terminals that are blocked for elongation by terminal transferase; (b) contacting the oligonucleotide probe to a solution containing a preselected base in the presence of terminal transferase to produce an extension product of the target nucleic acid, with the extension product comprised of the preselected base; (c) contacting the oligonucleotide probe to a transition metal complex that oxidizes the preselected base in an oxidation-reduction reaction; (d) detecting the presence or absence of the oxidation-reduction reaction; and (e) determining the presence or absence of the target nucleic acid in the test sample from the detected oxidation-reduction reaction at the preselected base. The test sample is preferably separated from the oligonucleotide probe prior to the detecting step, and is more preferably separated from the probe between steps (a) and (b) above. Separation may be carried out by use of an immobilized probe, or the probe may be provided free in solution, as discussed in section II above.

Oligonucleotide probes, hybridization methodology, oxidizing agents and oxidation-reduction reaction methods, detection of oxidation reduction reactions, and apparatus useful for carrying out these methods are as given in sections A–I above.

L. Sandwich Assays

Figure 8:
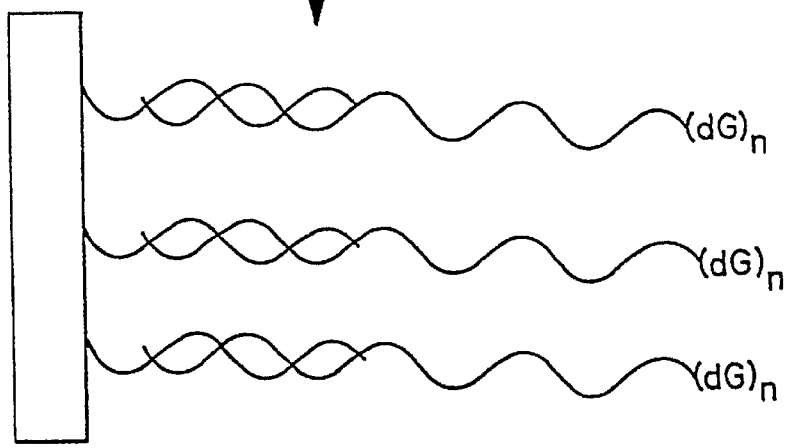
FIG. 8 schematically illustrates an alternate embodiment of the invention of FIG. 4, carried out in a sandwich assay format.
Figure 8:

A further embodiment of the method of section H above is the so-called "sandwich" assay, schematically illustrated in FIG. 8. In a sandwich assay, the target nucleic acid is part of a three (or more) member hybrid comprised of a capture probe, the target nucleic acid, and the signal probe.

A method of detecting the presence or absence of a target nucleic acid in a test sample suspected of containing the same, comprises: (a) providing an oligonucleotide capture probe, wherein the capture probe specifically binds to the target nucleic acid; (b) contacting the test sample to the capture probe to form a hybridized nucleic acid; (c) contacting an oligonucleotide signal probe to the hybridized nucleic acid, wherein the signal probe specifically binds to the target nucleic acid therein, and wherein the signal probe contains at least one preselected base, to produce a hybridized nucleic acid sandwich; (d) contacting the hybridized nucleic acid sandwich to a transition metal complex that oxidizes the preselected base in an oxidation-reduction reaction; (e) detecting the presence or absence of the oxidation-reduction reaction associated with the hybridized nucleic acid; and (f) determining the presence or absence of the target nucleic acid in the test sample from the detected oxidation-reduction reaction at the preselected base. The test sample is preferably separated from the capture probe, which separating step may occur between step (b) and step (c) above, or between step (c) and step (d) above. Depending on the assay format (e.g., heterogenous or homogenous), the oligonucleotide capture probe may be immobilized on a solid support (e.g., a polymeric bead, a plate, or the inside surface of a microtiter plate well), or alternate means provided for separating the hybridized nucleic acid from the test sample, as discussed above.

Numerous "sandwich" assay formats are known. The choice of assay format is not critical, and any suitable format may be employed to carry out the present invention. For example, the oligonucleotide capture probe may be immobilized on a solid support, as described in U.S. Pat. No. 4,486,539 to Ranki et al. The oligonucleotide probe may contain a polymer-forming unit, as described in U.S. Pat. No. 4,868,104 to Kurn et al., and the hybridized nucleic acid sandwich separated by polymerization thereof. The signal probe may be linear or branched, as described in M.S. Urdea, *Clinical Chem.* 39, 725–726 (1993). A mediator polynucleotide that binds the oligonucleotide capture probe to an immobilized polynucleotide, as described in U.S. Pat. No. 4,751,177 to Stabinsky, may be employed. The oligonucleotide probe may be joined to one member of a specific binding pair (e.g., biotin), and the hybridized nucleic acid sandwich separated from the test sample by means of a second binding interaction with the other member of the binding pair, that is immobilized on a solid support (e.g., avidin), as described in R. Goodson, EPO Application 0 238 332: W. Harrison, EPO Application 0 139 489, and N. Dattagupta, EPO Application 0 192 168.

Qligonucleotide probes, hybridization methodology, oxidizing agents and oxidation-reduction reaction methods, detection of oxidation reduction reactions, and apparatus useful for carrying out these methods are as given in sections A–K above.

M. Detection of Preselected Base in the Presence of Background Guanine Signal

The presence of a preselected base in an oligonucleotide probe may be detected even in the presence of background signal produced from the oxidation of guanine. Because the detection of mismatches relies upon the ability to detect a preselected base in the oligonucleotide probe in the presence of the the four native bases (A, T/U, C, and G). Therefore, the preselected base must be capable of being oxidized more rapidly than the other four bases.

The present invention provides an oligonucleotide probe useful for the electrochemical detection of a preselected base in the presence of background guanine signal. The oligonucleotide probe may consist of any oligonucleotide probe as given in section B above, where at least one purine base in the oligonucleotide probe is a purine substituent of Formula I:

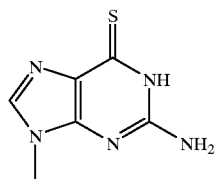

The oligonucleotide probe may contain as many bases of the foregoing formula as desired (e.g., 1, 2 or 3 up to 5, 10, or 15 or more) depending on the intended binding partner thereof. Specific examples of such oligonucleotide probes, and nucleotides useful for the preparation thereof, are compounds of Formula II:

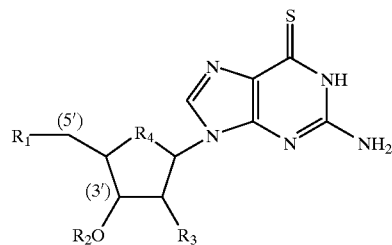

wherein:
  $R_1$ is HO—P(O)(OH)—O—, a nucleotide, or an oligonucleotide;
  $R_2$ is —H, a nucleotide or an oligonucleotide;
  $R_3$ is —H, —OH, halo (e.g., fluoro, chloro), alkoxy (e.g., Cl–C4 alkoxy such as methoxy or ethoxy), amino, or azido; and $R_4$ is —O— or —CH$_2$—.

Oligonucteotide probes as described in connection with Formulas I and II above are made in accordance with known techniques, modified in light of the Examples set forth below, as will be readily apparent to those skilled in the art.

In one preferred embodiment of the compound of Formula II, $R_1$ is HO—P(O)(OH)—O—. In another preferred embodiment of the compound of Formula I, R is —H. When $R_1$ is a nucleotide or an oligonucleotide, the phosphodiester bond is to the 3' terminus. When $R_2$ is a nucleotide or oligonucleotide, the phosphodiesther bond is to the 5' terminus.

The compounds of Formula I are advantageously included as a base in an oligonucleotide probe which may be utilized in the methods of the present invention, as described in sections A–M above. The oligonucleotide probe may of course include multiple bases, but should include at least one base of Formula I when the oligonucleotide probe is to be used for the detection of a preselected base in the presence of background guanine. The oligonucleotide probe may be 5, 10, 50 or up to 100 base pairs in length. A particular example of a compound of Formula II is 6-mercaptoguanosine 5'-monophosphate (6-S-GMP).

N. Electrode Structures

An electrode useful for the electrochemical detection of a preselected base in a nucleic acid in accordance with the methods described above comprises: (a) a conductive substrate having a working surface formed thereon; and (b) a polymer layer connected to the working surface. The polymer layer is one that binds the nucleic acid (e.g., by hydrophobic interaction or any other suitable binding technique) and is porous to the transition metal complex (i.e., the transition metal complex can migrate to the nucleic acid bound to the polymer). The conductive substrate may be a metallic substrate or a non-metallic substrate, including semiconductor substrates (e.g., gold, glassy carbon, indium-doped tin oxide, etc.). The conductive substrate may take any physical form, such as an elongate probe having a working surface formed on one end thereof, or a flat sheet having the working surface formed on one side thereof. The polymer layer may be connected to (he working surface by any suitable means, such as by clamping the polymer layer to the working surface, evaporation of a solution of the polymer onto the electrode, or electropolymerization. Exemplary polymers include, but are not limited to, nylon, nitrocellulose, polystyrene, and poly(vinylpyridine). The thickness of the polymer layer is not critical, but can be from 100 Angström (Å) to 1, 10, or even 100 microns. The electrode may be used in essentially all of the methods described in sections A–M above. Thus, in general, the present invention provides a method of detecting a nucleic acid, said nucleic acid containing at least one preselected base, the method comprising: (a) contacting a sample containing said nucleic acid to an electrode, the electrode comprising a conductive substrate having a working surface formed thereon and a polymer layer as described above connected to the working surface; (b) reacting the nucleic acid with a transition metal complex capable of oxidizing the preselected base in an oxidation-reduction reaction: (c) detecting said oxidation-reduction reaction by measuring current flow through said electrode; and (d) determining the presence or absence of the nucleic acid from the detected oxidation-reduction reaction at the preselected base.

O. Microelectronic Devices

An advantage of the techniques described above is that they may he carried out with a microelectronic device. A microelectronic device useful for the electrochemical detection of a nucleic acid species in the methods described above comprises a microelectronic substrate having first and second opposing faces; a conductive electrode on the first face; and an oligonucleotide capture probe immobilized on the first face adjacent the conductive electrode. The capture probe is spaced sufficiently close to the adjacent electrode (e.g., from about 0. 1, 1, or 2 $\mu$ up to about 50, 100, 500 or even 1000$\mu$) so that an oxidation reduction reaction occuring at that probe, or at a target nucleic acid hybridized to that probe, is detected at the adjacent electrode.

Figure 9:
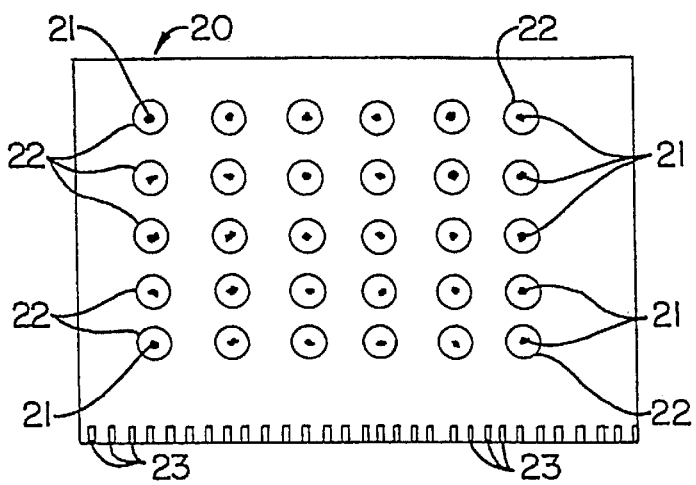
FIG. 9 is a schematic illustration by top plan view of a microelectronic device useful for carrying out methods of the present invention.
Figure 10:
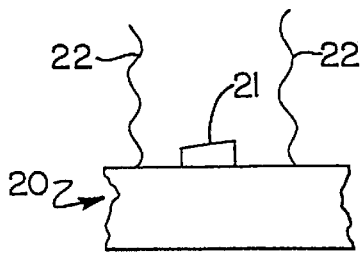
FIG. 10 is a side sectional view of a portion of the device illustrated in FIG. 9.

In the preferred embodiment illustrated in FIG. 9 and FIG. 10, a micrelectronic device 20 has a plurality of separate electrodes 21 on the first opposing face, and a plurality of separate oligonucleotide capture probes 22 immobilized adjacent to each of the separate electrodes. By providing a plurality of separate oligonucleotide probes, differing from one another, each with an associated electrode, a single, compact device is provided that can detect a variety of different hybridization events. Each electrode is electrically connected to a suitable contact 23 so that the device may be wired or otherwise operatively associated with the necessary electronic equipement for carrying out the detection and determining steps of the methods described herein.

The nucleic acid may be selectively immobilized at the appropriate location on the microelectronic substrate by known techniques. See, e.g., U.S. Pat. No. 5,405,783 to Pirrung et al. The microelectronic substrate may be a semiconductor (e.g., silicon) or non-semiconductor materials that can be processed using conventional microelectronic techniques (e.g., glass). The electrode may be metal or a non-metallic conductive material, such as polycrystalline silicon. The electrode can be formed using conventional microelectronic processing techniques, such as deposition etching. A variety of suitable microelectronic structures and fabrication techniques are well known to those skilled in the art. See, e.g., S. M. Sze, *VLSI Technology* (1983); S. K. Ghandhi, *VLSI Fabrication Principles* (1983).

The following examples are provided to illustrate the present invention, and should not be construed as limiting thereof. In these examples, cm$^2$/s means centimeters squared per second, M means molar concentration, M$^{-1}$s$^{-1}$ means per molar per second, eV means electron volts, V means volts, nm means nanometers, GMP means guanosine 5'-monophosphate, and ITO means tin-doped indium oxide electrode. Cyclic voltammograms were collected with an EG+G Princeton Applied Research Potentiostat/Galvanostat, Model 273A, in accordance with known techniques. ITO working electrodes are fabricated from an ITO-coated soda-lime glass sheet, part number CH-50IN-1514, available from Delta Technologies, Ltd, 13960 North 47th Street, Stillwater, Minn. 55082–1234 USA. Nylon film is available as HYBOND-N+ nylon membrane, catalog no. RPN 1210B, from Amersham Corp, 2636 Clearbrook Drive, Arlington Heights, Ill. 60005 USA.

EXAMPLE 1

Measurement of Cyclic Voltammogram of Ru(bpy)$_3^{2+}$

The cyclic voltammograms of Ru(bpy)$_3^{2+}$ with and without calf thymus DNA are shown in FIG. 1, with the catalytic enhancement produced by the muiltiple turnovers of oxidation of DNA by the oxidized form of the metal complex which are observed during a single voltammetry sweep. The voltammetry of any DNA-bound redox couple must be analyzed in terms of a square-scheme that relates the bound and unbound forms because the diffusion coefficient of DNA is much lower (i.e., 2.0×10$^{-7}$ cm$^2$/s) than that of the metal complex (8.0×10$^{-6}$ cm$^2$/s). This phenomenon generally leads to dramatically decreased currents for the bound form; however, at sufficient high ionic strength ([Na$^+$]=0.8 M), binding of the metal complex is too weak to influence the current response. In this case, the current can be analyzed in terms of a simple EC' mechanism.

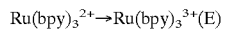

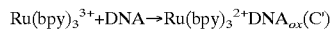

EXAMPLE 2

Analysis of Cyclic Voltammograms

Cyclic voltammograms were analyzed by fitting the complete current-potential curves, with the background subtracted, using the DIGISIM™ data analysis package. The input parameters were E$_{1/2}$ for the metal complex and the diffusion coefficients for the metal complex and the DNA, all of which were determined in separate experiments. Therefore, the sole parameter obtained from the fit was the second-order rate constant for equation 2, k=9.0×10$^3$ M$^{-1}$s$^{-1}$. This same rate constant was determined over a wide range of scan rates.

The rate constant for oxidation of DNA by Ru(bpy)$_3^{3+}$ was confirmed in two separate experiments. First, square-wave voltammograms were used to obtain a pseud(l-first-order k$_{obs}$ for equation 2 by fitting with the COOL™ algorithm. The COOL™ algorithm uses a fitting approach that is significantly different from DIGISIM™; nevertheless, plots of k$_{obs}$ against DNA were linear and gave a second-order rate constant k=8.2×10$^3$ M$^{-1}$s$^{-1}$, which is in agreement with the rate constant obtained from fitting cyclic voltammograms with DIGISIM™. Second, authentic samples of Ru(bpy)$_3^{3+}$ were prepared and reacted with DNA directly in a rapid-scanning stopped flow. Global analysis of the time-dependent spectral between 350 and 600 nm showed that Ru(bpy)$_3^{3+}$ was converted cleanly to Ru(bpy)$_3^{2+}$ with no intermediates and a rate constant of 12×10$^3$ M$^{-1}$s$^{-1}$. Thus, the rate constant for DNA oxidation by Ru(bpy)$_3^{3+}$ was firmly established by two independent electrochemical measurements with dramatically different fitting protocols and by a non-electrochemical stopped flow technique with fitting of the complete visible spectra.

EXAMPLE 3

Analysis of Cyclic Voltammograms

If the driving force for electron transfer is significantly less than the reorganizational energy ($\lambda$), a plot of RT ln k versus driving force (when corrected for work terms associated with approach of the reactants) should yield a straight line with a slope of ½. The rate constants for oxidation of DNA by a number of Metal(bpy)$_3^{3+}$ derivatives with different redox potentials are shown in Table 1 below.

Since Marcus theory describes the driving-force dependence of the electron-transfer rate, absolute rate constants can be analyzed in terns of the following equation:

$$k = \nu \exp[-\beta(r-r_0)] \exp[-(\Delta G + \lambda)^2/4\lambda RT]$$

where $\nu$ is the rate constant in the diffusion-controlled limit ($10^{11}$ M$^{-1}$s$^{-1}$), r is the distance between reactant and product in the activated complex, $r_0$ is the distance of closest approach of reactant and product, and $\beta$ describes the influence of the intervening medium. Incorporation of the guanine donor into the interior of the double helix imposes a finite distance across which the electron must tunnel to the Docked metal complex, i.e., $r/r_0$. However, if guanosine 5'-monophosphate (GMP) is used as the electron donor, direct collision of guanine with the metal complex is possible ($r = r_0$). For Fe(bpy)$_3^{3+}$ and GMP, the rate constant measured by stopped-flow is $2.6 \times 10^3$ M$^{-1}$s$^{-1}$. Known values of $\lambda$ for related reactions are in the range 1–1.5 eV, which give a $\Delta G$ for the guanine$^{+/0}$ couple of $1.1 \pm 0.1$ V.

TABLE 1

Rate Constants for Oxidation of Guanine in DNA Oligomers by Ru(bpy)$_3^{2+}$

| k(M$^{-1}$s$^{-1}$)[a] | oligomer sequence | $\Delta r_{Ru-G}$(Å)[b] |
|---|---|---|
| $1.2 \times 10^3$ | (5'-AAATATAGTATAAAA) · (3'TTTATATCATATTTT) GC pair | 1.7Å |
| $5.1 \times 10^3$ | (5'-AAATATAGTATAAAA) · (3'-TTTATATTATATTTT) GT mismatch | 1.2Å |
| $1.0 \times 10^{4c}$ | (5'-AAATATAGTATAAAA) · (3'-TTTATATGATATTTT) GG mismatch | 1.0Å |
| $1.9 \times 10^4$ | (5'-AAATATAGTATAAAA) · (3'-TTTATATAATATTTT) GA mismatch | 0.7Å |
| $1.8 \times 10^5$ | (5'-AAATATAGTATAAAA) single strand | 0Å |
| $5.1 \times 10^3$ | (5'-AAATATAGTATAAAA · (3'-TTTATATCTATTTT) | 1.2Å |

[a]DNA concentrations used to determine rate constants were based on the moles of guanine nucleotides.
[b]Estimated distance of tunneling through solvent. Distances calculated according to k/k$_{ss}$ = exp[-$\beta\Delta$r], where $\beta$(H$_2$O) = 3A $^1$and k$_{ss}$ = 1.8 × 10$^5$M$^{-1}$s$^{-1}$.
[c]Since the rate constants are relative to guanine concentrations. the observed rate for the GG mismatch has been normalized relative to the other oligomers containing a single guanine.

Figure 2:
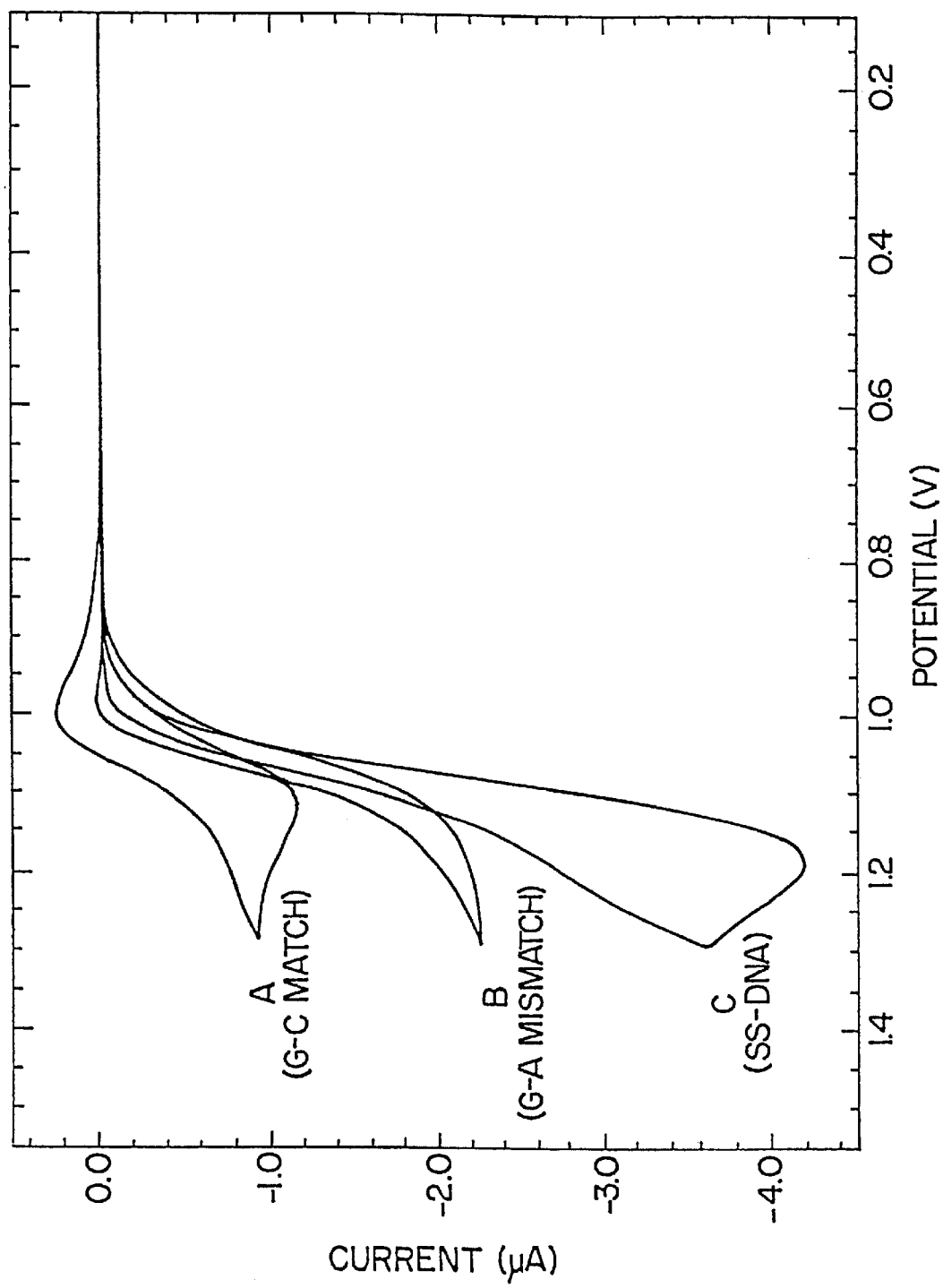
FIG. 2 shows the cyclic voltammograms of $Ru(bpy)_3^{2+}$ in the presence of 5'-AAATATAGTATAAAA as a single strand (C) and hybridized to complementary strands (A & B). The scan rate is 25 mV/s. (A) represents 25 $\mu$M $Ru(bpy)_3^{2+}$+100 $\mu$M (in guanine nucleotides) double stranded fully hybridized DNA (5'-AAATATA$\underline{G}$TATAAAA).(3'-TTTATAT$\underline{C}$ATATTTT). (B) represents $Ru(bpy)_3^{2+}$ with a duplex containing a GA mismatch (5'-AAATATA$\underline{G}$TATAAAA).(3'-TTTATAT$\underline{A}$ATATTTT), and (C) represents $Ru(bpy)_3^{2+}$ a single strand containing one guanine nucleotide (5'-AAATATA$\underline{G}$TATAAAA).

In FIG. 2 are the cyclic voltammograms or Ru(bpy)$_3^{2+}$ in the presence of 5'-AAATATAGTATAAAA as a single stand (C) and hybridized to its complementary strand (A). As with GMP, $r = r_0$ for the single strand, and the rate constant of $1.8 \times 10^5$ M$^{-1}$s$^{-1}$ gives $\Delta G$(guanine$^{+/0}$)=1.1 V and $\lambda$=1.3 eV, which are in agreement with the values from GMP oxidation. While there is a dramatic enhancement for the single strand, only a slight enhancement is observed for the fully hybridized duplex at this scan rate, resulting in a four-fold reduction in current upon hybridization. Metal complexes such as Ru(bpy)$_3^{2+}$ are known to Dock to DNA in the minor groove, so the 150-fold slower rate constant ($1.2 \times 10^3$ M$^{-1}$s$^{-1}$) for oxidation of the duplex must result from the distance between the guanine residue and the surface-bound complex. When the metal complex is docked in the minor groove, guanine and the metal complex cannot come into intimate contact, and the electron must tunnel through the solvent that separates the guanine residue and the metal complex. Tunneling through water is much less efficient than through non-polar media, and the value of $\beta$ for water is estimated to be about 3 Å$^{-1}$. The tunneling distance can therefore be calculated according to:

$$k/k_{ss} = \exp(-\beta\Delta r)$$

where $\Delta r$ is the change in distance in the duplex compared to the single strand. From this analysis, $\Delta r$ for the fully hybridized duplex is 1.7 Å.

The large value of $\beta$ for water suggests that significant changes in the electron-transfer rate constants will be effected by very small changes in the tunneling distance, which could in turn reflect small perturbations in the DNA structure. Also shown in FIG. 2 is the voltammogram of Ru(bpy)$_3^{2+}$ in the presence of the same duplex where the GC base pair has been replaced by a GA mismatch. Incorporation of the GA mismatch results in a two-fold enhancement in the raw current compared to the authentic duplex, which translates to a 16-fold change in rate constant (k$_{GA}$=1.9×10$^4$ M$^{-1}$s$^{-1}$). The rate data for the single strand, fully hybridized duplex, and all three GX mismatches are set out in Table 1. Also shown are the calculated tunneling distances $\Delta r$ relative to the single strand. As expected, the guanine residue in G-purine mismatches is more accessible to the metal complex than in the GT mismatch where the two bases are still joined by two hydrogen bonds in a wobble pair. Nonetheless, the GT mismatch still causes a 4-fold change in the rate constant, which is readily detectible. Therefore, the oxidation rate constants follow the trend G (single strand)>GA>GG>GT>GC. The ability to distinguish each of these mismatches from one another, provides the basis for mismatch-sensitive detection of hybridization which is sensitive even to single-base pair mismatches at the base pair adjacent to the preselected base.

EXAMPLE 4

Figure 5:
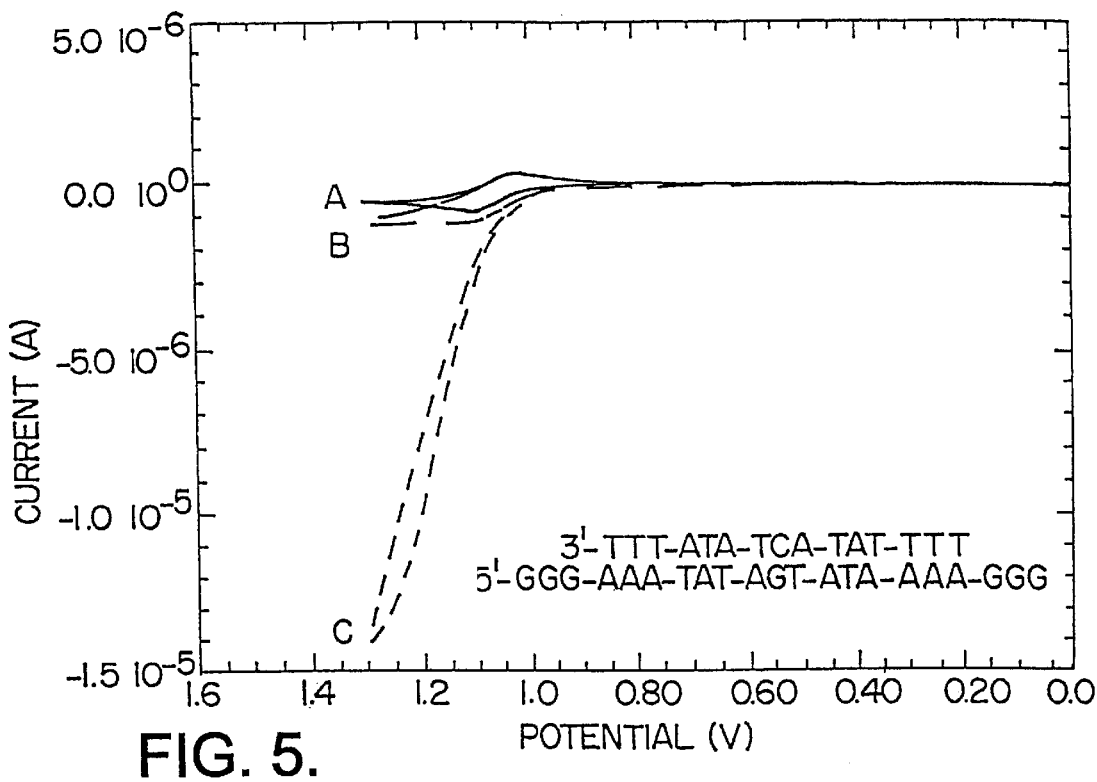
FIG. 5 shows the cyclic voltammograms of $Ru(bpy)_3^{2+}$ (25 $\mu$M) at a scan rate of 25 mV/s in 50 mM sodium phosphate buffer with 0.7 M NaCl, pH 7. (A) No added oligonucleotide. (B) With 75 $\mu$M d[5'-TTTTATACTATATTT]. (C) With 75 $\mu$M of the hybrid of the oligomer from B and d[5'-GGGAAATATAGTATAAAAGGG]. Working electrode: tin-doped indium oxide. Reference electrode: Ag/AgCl. Counter electrode: Pt wire. The secondary structure of the hybrid from C is indicated on the Figure.
Figure 6:
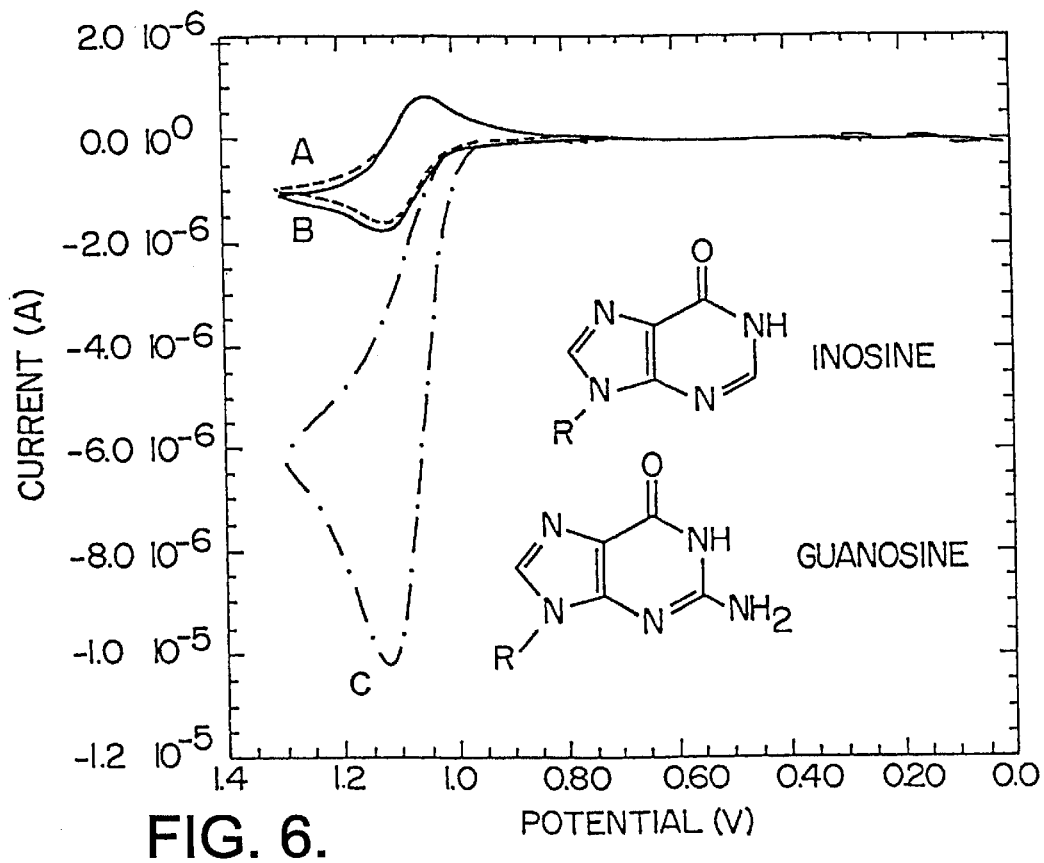
FIG. 6 shows the cyclic voltammograms of (A) $Ru(bpy)_3^{2+}$ (25 $\mu$M), (B) $Ru(bpy)_3^{2+}$ (25 $\mu$M) with inosine 5'-monophosphate (0.3 mM), and (C) $Ru(bpy)_3^{2+}$ (25 $\mu$M) with guanosine 5'-monophosphate. Structures of inosine and guanine are shown in the Figure.

Modified Bases to Avoid Oxidation in Probe Strand: Substitution of Inosine for Guanine Cyclic voltammograms were collected using an indium tin oxide (ITO) working electrode (area=0.32 cm$^2$), Pt-wire counter electrode, and an Ag/AgCl reference electrode. In FIG. 5, a sample containing 25$\mu$M Ru(bpy)$_3^{2+}$ and 75 $\mu$M oligonucleotide dissolved in 50 mM Na-phosphate buffer (pH 7) with 0.70 M NaCl was scanned at 25 mV/s In FIG. 6, a sample containing 50 $\mu$M Ru(bpy)$_3^{2+}$ and 0.3 mM of either 5'-GMP or 5'-IMP dissolved in buffered aqueous solutions containing 700 mM NaCl and 50 mM Na-phosphate buffer (pII=6.8, [Na$^+$]=780 mM) was scanned at 2.5 mV/s from 0.0 V to 1.3 V. Scans of mononucleotides in the absence of Ru(bpy)$_3^{2+}$ showed no appreciable oxidative current. A freshly-cleaned ITO electrode was used for each experiment, and a background scan of buffer alone subtracted from subsequent scans. Second-order guanine oxidation rate constants were determined by fitting of cyclic voltammetric data to a two-step mechanism using the DIGISIM™ software package. All parameters other than the oxidation rate were determined from a voltammograms of the metal complex alone on the same electrode. The 5'-GMP was purchased from Sigma and the 5'-IMP was purchased from U.S. Biochemical, and both were used without further purification. Oligonucleotides were prepared in the UNC Department of Pathology and passed through a 3000-molecular weight cutoff filter to remove mononucleotides. Purity was assessed by reverse-phase HPLC. The concentration was determined from the optical absorption at 260 nm as described in Fasman, G.D. *CRC Handbook of Biochemistry and Molecular Biology*; CRC Press, Boca Raton, Fla, 1975; Vol. 1. The hybrid in FIG. 5 was prepared by heating the complementary strands of 90° C. for 5 min and slowly cooling to 25° C. over 2 h.

These data indicate that inosine may be substituted for guanine in the probe strand to provide a redox inactive probe strand.

EXAMPLE 5

Modified Bases to Avoid Oxidation in Probe Strand: 7-Deaza-Guanine

This example is carried out in essentially the same manner as example 4 above, except that 7-deaza-guanine is used as the modified base as an alternative to guanine to provide a redox-inactive probe strand.

7-deaza-guanine is oxidized at a rate of only $10^3$ $M^{-1}s^{-1}$, which is two orders of magnitude slower than guanine and is sufficiently slow to provide a redox-inactive probe strand.

EXAMPLE 6

Detection Using Calf Thymus DNA Bound to Nylon Membrane Attached to ITO Electrode Nylon film is cut into a circular shape, approximately 6 mm in diameter so as to fit into the electrochemical cell and cover the portion of the ITO electrode exposed to the solution.

For the experiments in which only the cyclic voltammogram of the metal complex is obtained, the ITO electrode is first conditioned with buffer. The nylon disk (no DNA) is then inserted into the electrochemical cell and 200 µL of a 200 µM metal complex solution is pipetted into the cell. For the $Os(bpy)_3^{2+}$ experiments, an equilibration time of 6 minutes is used prior to electrochemical analysis. For the $Ru(bpy)_3^{2+}$ experiments, an equilibration time of 15 minutes is used prior to electrochemical analysis. Cyclic voltammograms are collected using an PAR 273A potentiostat at a scan rate of 25 mV/s.

For the DNA experiments, the DNA-soaked nylon disk is inserted into the electrochemical cell after conditioning of the ITO electrode in the appropriate buffer. 200 µL of a 200 µM metal complex solution in the appropriate buffer is pipetted into the cell, and a cyclic voltammogram is taken after the appropriate equilibration time (6 minutes for $Os(bpy)_3^{2+}$ and 15 minutes for $Ru(bpy)_3^{2+}$) at a scan rate of 25 mV/s. The nylon disks are soaked for approximately 5 minutes in a solution of 5.8 mM calf thymus DNA dissolved in water. A variety of soak times were investigated ranging from 5 minutes to 18 hours. The DNA rapidly (within minutes) associates with the nylon film, so short soak times are typically employed. Under low salt conditions, a 50 mM Na-phosphate buffer (pH=6.8, [Na$^+$]=80 mM) is used. Under high salt conditions, a 50 mM Na-phosphate buffer and 700 mM NaCl (pH=6.8, [Na$^+$]=780 mM) solution is used.

Figure 11:
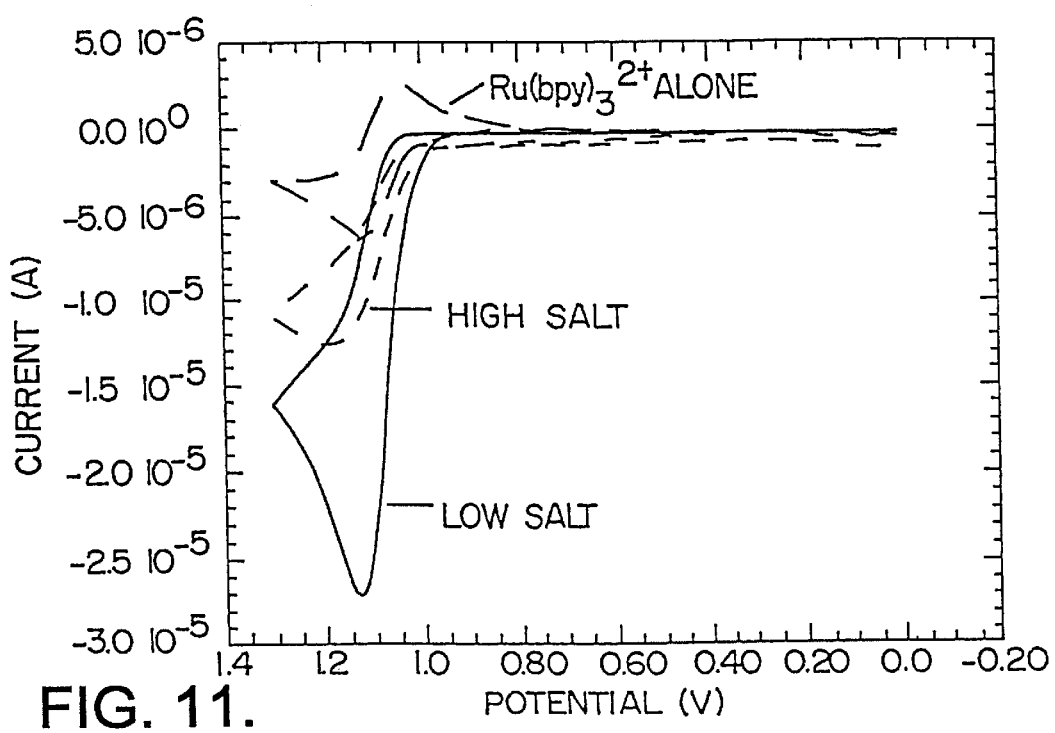
FIG. 11 shows the cyclic voltammograms using nylon-modified ITO electrodes, of $Ru(bpy)_3^{2+}$ (200 $\mu$M) at buffer-soaked nylon, $Ru(bpy)_3^{2+}$ (200 $\mu$M) at DNA-soaked nylon in high salt (700 mM added NaCl) buffer, and $Ru(bpy)_3^{2+}$ (200 $\mu$M) at DNA-soaked nylon in low salt (i.e., no added NaCl) buffer.

The cyclic voltammogram of $Ru(bpy)_3^{2+}$ at the nylon-ITO electrode is shown in FIG. 11. The dashed line shows the voltammogram when the nylon membrane is soaked in calf thymus DNA prior to attachment to the electrode. There is a large catalytic current for the DNA-labelled membrane that parallels that observed in solution. The experiment demonstrates that $Ru(bpy)_3^{2+}$ diffuses freely in the nylon film and that diffusion of the DNA is not required to realize the catalytic current. FIG. 11 also shows that a greater catalytic current is observed at lower salt concentrations, due to enhanced interaction between the mediator and the immobilized DNA.

Figure 12A:
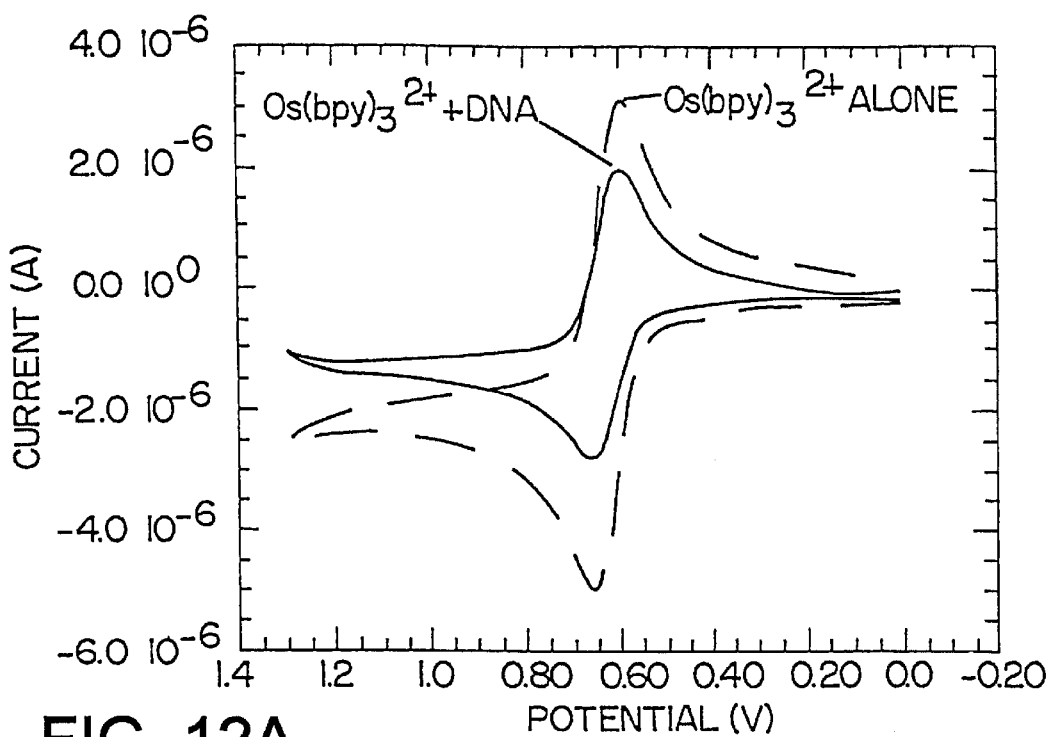
FIG. 12A shows the cyclic voltammogram with 700 mM NaCl added.
Figure 12B:
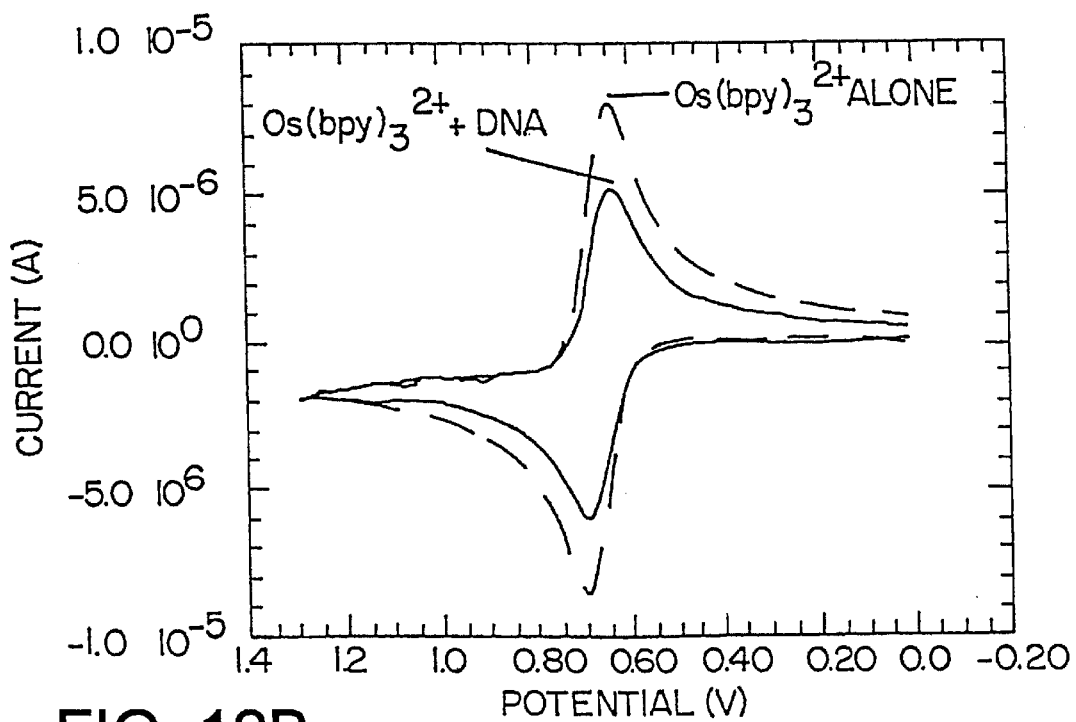
FIG. 12B shows the cyclic voltammogram with no NaCl added.

FIG. 12A shows the same experiment using $Os(bpy)_3^{2+}$ as the mediator. The osmium complex does not oxidize guanine, so any current enhancement observed in the presence of guanine would have to arise from preconcentration of the mediator due to DNA binding. In fact, the current for $Os(bpy)_3^{2+}$ is lower in the presence of DNA at the nylon electrode than in the absence of DNA. The experiment demonstrates that the increased current for $Ru(bpy)_3^{2+}$ when DNA is bound to the nylon electrode is solely due to the proprietary catalytic reaction and not due to a trival binding difference. The effect of salt concentration is shown in FIG. 12B, and is observed to be small compared to the large salt effect observed for the catalytic reaction.

By binding the DNA to the nylon membrane attached to the ITO electrode, we have demonstrated that DNA may be detected even in the embodiment wherein the DNA is not diffusing but the mediator is. This finding permits the detection of DNA where the immobilized probes are sufficiently close to the electrode so that the probe-target hybrids reside in the diffusion layer of the mediator.

EXAMPLE 7

Detection of RNA Bound to Nylon Membrane Attached to ITO Electrode

The experiment is carried out as described in Example 6, except that tRNA from Bakers Yeast (purchased from Sigma) is used instead of calf thymus DNA. A nylon film disk was soaked in a solution of tRNA as described in Example 6.

Figure 13:
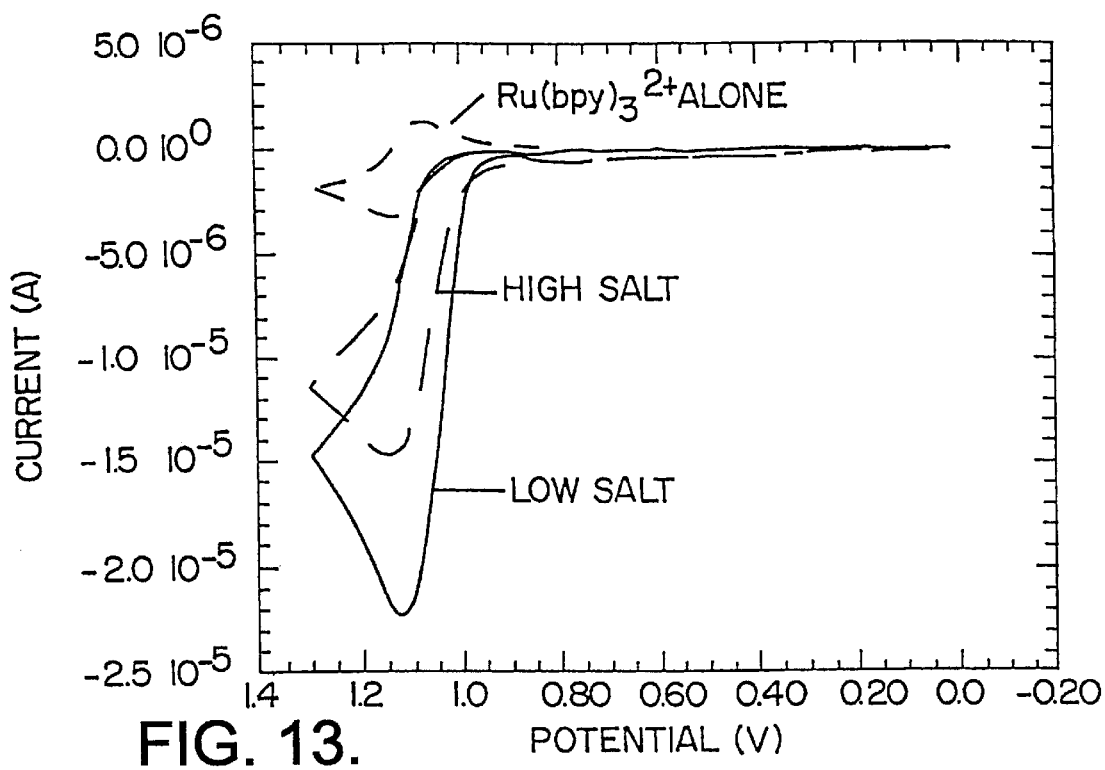
FIG. 13 shows the cyclic voltammograms at nylon-modified ITO electrodes showing cyclic voltammograms of $Ru(bpy)_3^{2+}$ (200 $\mu$M) at buffer-soaked nylon, $Ru(bpy)_3^{2+}$ (200 $\mu$M) at tRNA-soaked nylon in high salt (700 mM added NaCl) buffer, and $Ru(bpy)_3^{2+}$ (200 $\mu$M) at tRNA-soaked nylon in low salt (no added NaCl) buffer.

The cyclic voltammetry in the presence of $Ru(bpy)_3^{2+}$ is shown in FIG. 13. As with DNA, catalytic current is observed for both buffers with more current at low salt. The difference observed in current between the high and low salt concentrations is not as dramatic as that observed with DNA in Example 6 because tRNA does not bind cations as well as DNA and therefore the salt effects are less dramatic.

The results in FIG. 13 demonstrate that RNA can be detected in a manner identical to that for DNA, which occurs because both RNA and DNA contain guanine. The chemical composition of the sugar-phosphate backbone therefore does not influence the catalytic current. Based upon this observation, the detection of both single- and double-stranded DNA and RNA, DNA-RNA hybrids, as well as single strands or duplexes containing other modified backbones such as PNA's, carbocycles, phosphorothioates, or other substituted ribose linkages is possible.

EXAMPLE 8

Detection of RNA

For quantitative detection of RNA, a DNA (or RNA, PNA, or other alternative backbone) probe is immobilized on a solid support. The probe may be modified to be redox-inert by substitution of inosine or 7-deaza-guanine for the guanines in the probe strand. The immobilized probe is then contacted with a solution of target RNA (for example from HIV or Hepatitis C). The solid surface then contains a redox-inert, immobilized probe hybridized to a strand of RNA. The solid surface is then contacted with a solution of Ru(bpy)$_3^{2+}$, and the cyclic voltammogram of the mediator is measured. The catalytic current signals the hybridization event, and the magnitude of the current is used to quantitate the bound RNA strand based upon the known number of guanines in the strand.

For the mismatch detection of RNA, a DNA (or RNA, PNA, or other alternative) probe is immobilized to a solid surface. The preselected base in the probe strand is oxidized more easily than the other bases. The surface is contacted with a solution of target RNA and then contacted with a solution of Ru(bpy)$_3^{2+}$ or other mediator. The extent of hybridization (perfect match, no pairing, or mismatch) is then determined at the preselected base in the same manner as for DNA.

EXAMPLE 9

Detection of a Preselected Sequence of Bases

Figure 14:
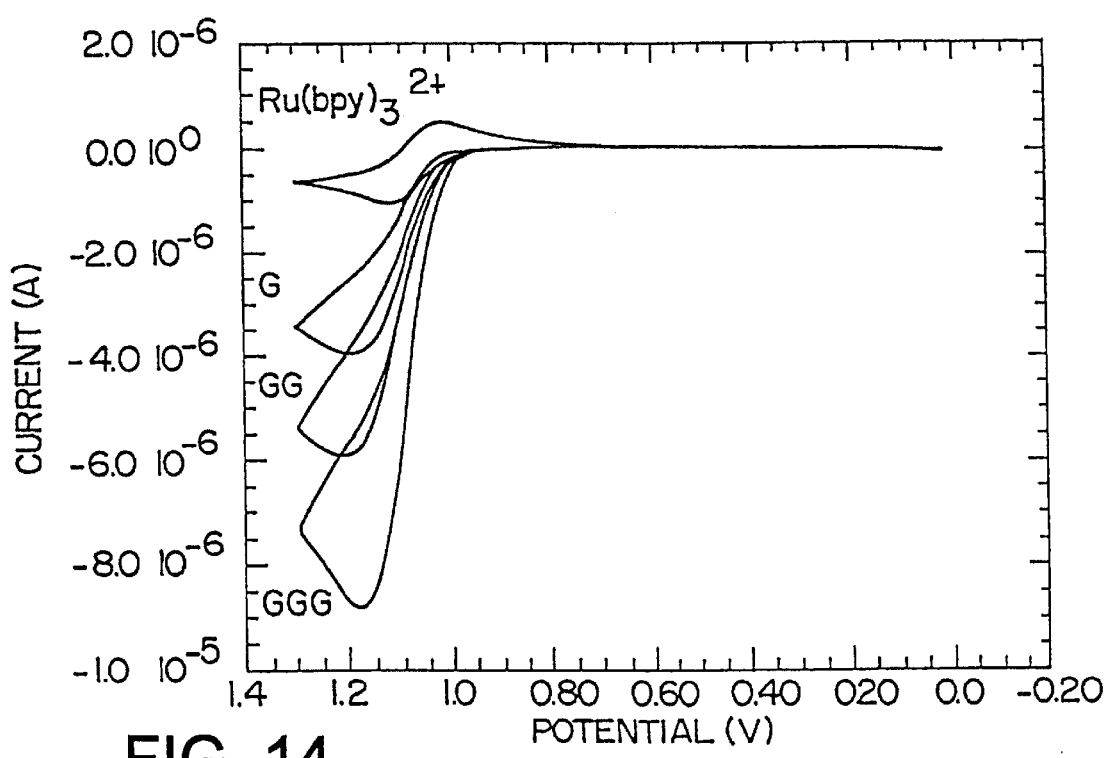
FIG. 14 shows the cyclic voltammogram of $Ru(bpy)_3^{2+}$ (25 $\mu$M) alone and with (100 $\mu$M in strands) of 5'-AAATATAG$_n$TATAAAA where n=1 (G), 2 (GG), or 3 (GGG). The scan rate is 25 mV/s.
Figure 15:
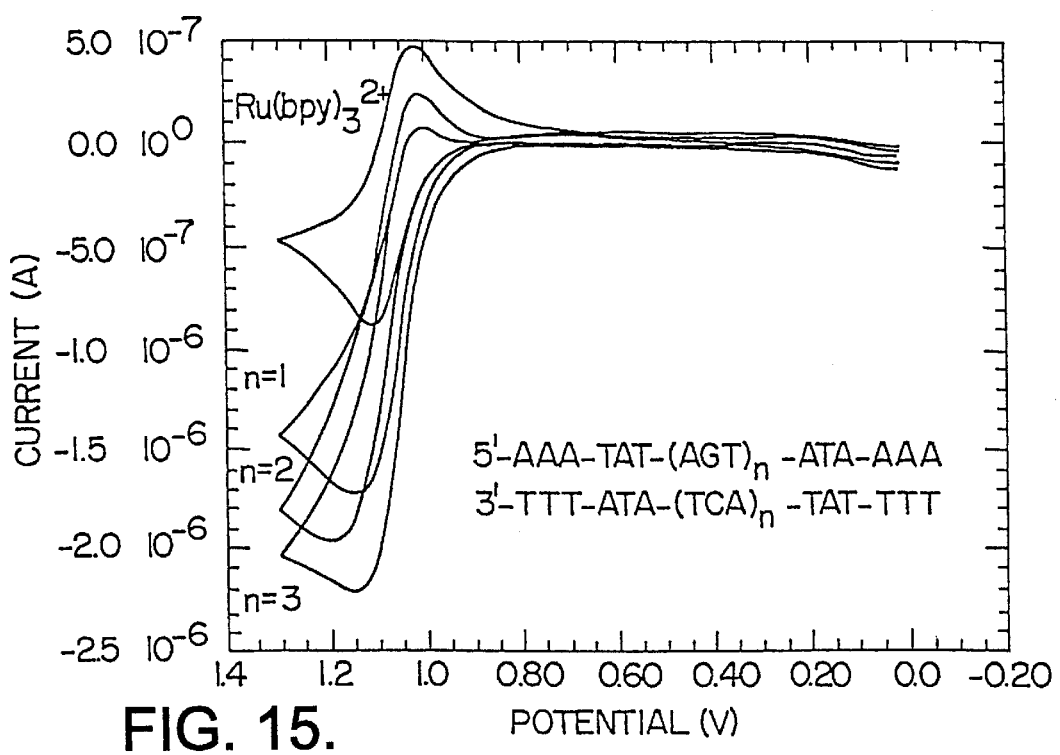
FIG. 15 shows the cyclic voltammogram of $Ru(bpy)_3^{2+}$ (25 $\mu$M) alone and with (100 $\mu$M in strands) of 5'-AAATAT (AGT)$_n$ATAAAA where n=1, 2, or 3. The scan rate is 25 mV/s.

The method was carried out as described in Example 3. The cyclic voltammograms set forth in FIG. 14 demonstrate that the current due to 5'-G is much less than that for 5'-GG which is much less than that for 5'-GGG. This tremendous increase in current is observed for both single strands and duplexes that contain GG and GGG sequences. The increase in current is not due simply to the increase in the number of G's, because as shown in FIG. 15, the increase in current due to adding G's to the same strand is much lower if the G's are interspersed. Since the 5'-G of the GGG is much easier to oxidize than a single G, it is possible to select a mediator (with a lower redox potential) that is capable of oxidizing GGG but not G.

Figure 16:
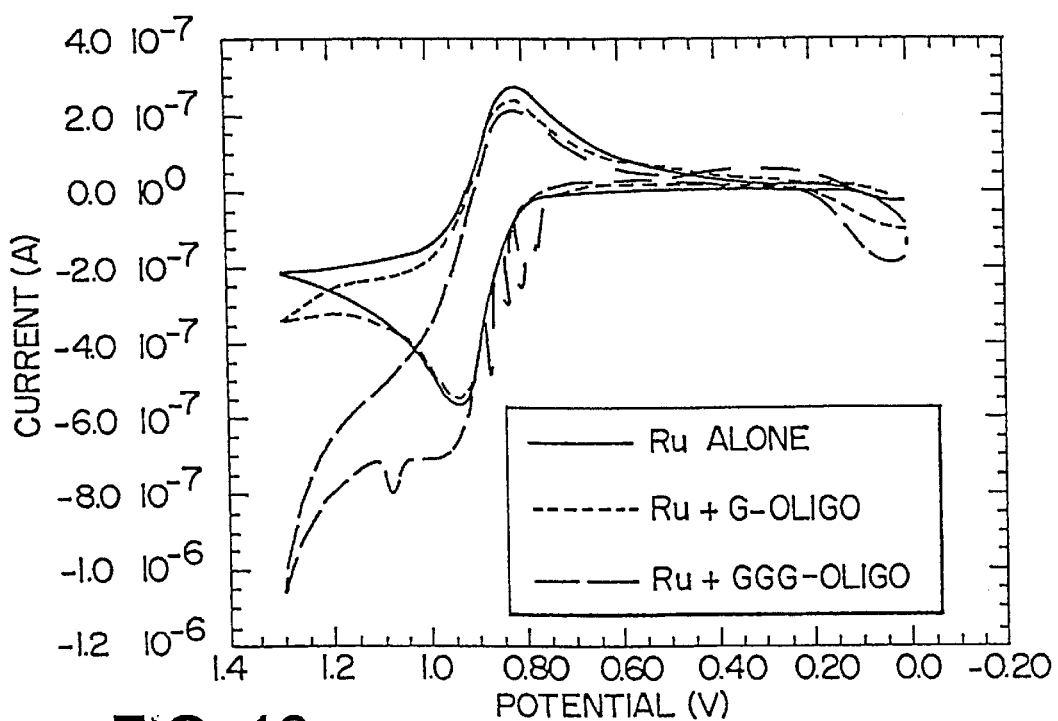
FIG. 16 shows the cyclic voltammogram of 25 $\mu$M Ruthenium(4,4'-dimethylbipyridine)$_3^{2+}$ (or "$Ru(4,4'-Me_2-bpy)_3^{2+}$") alone (solid) and with (100 $\mu$M in strands) of 5'-AAATATAGTATAAAA (dotted) and 5'-AAATATAGGGTATAAAA (dashed). The scan rate is 25 mV/s.

The cyclic voltammogram of Ru(4,4'-dimethyl-bipyridine)$_3^{2+}$ is shown in FIG. 16 along with repeat scans in the presence of the single G oligonucleotide and the GGG oligonucleotide. As shown, catalytic current is observed only in the presence of the GGG oligonucleotide. This example shows the ability to tune the potential of the mediator such that a more easily oxidized sequence can be detected in the presence of background guanine. The same strategy can be applied to detecting a single synthetic base that is derivatized to make it more easily oxidized than guanine.

The experiment demonstrates that it is possible to lower the potential of the mediator and still distinguish a more easily oxidizable base or base sequence.

EXAMPLE 10

Detection of a Preselected Guanine Derivative in the Presence of Background Native Guanine The disodium salt of 6-mercaptoguanosine 5'-monophosphate (6-S-GMP)

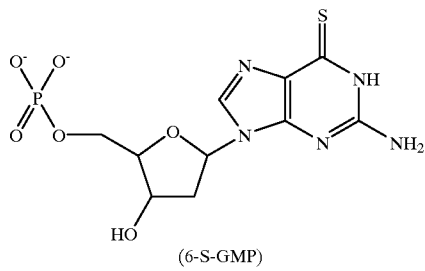

(6-S-GMP)

is prepared by phosphorylation of commercially available 6-mercaptoguanosine (from Sigma). The phosphorylation is performed using POCl$_3$ according to the procedure of M. Yoshikawa, et al., Bull. Chem. Soc. Jpn. 42:3505 (1969). The disodium salt of 6-S-GMP is purified by HPLC prior to voltammetric analysis. Cyclic voltammograms are performed at high ionic strength as in the inosine-5'-monophosphate example. The working electrode is a ITO with a Hybond N+ nylon membrane attached to the surface to prohibit direct oxidation of the 6-S-GMP. The counter electrode is a Pt wire. The reference electrode is Ag/AgCl. The scan rate is 25 mV/s.

Figure 17:
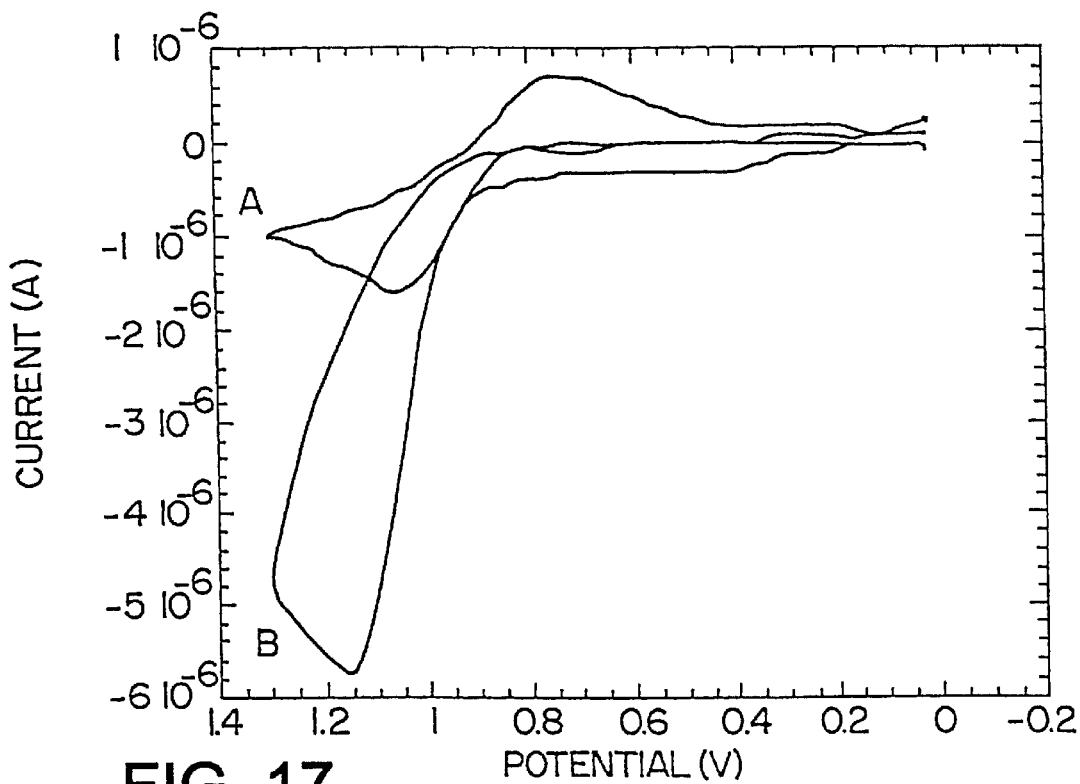
FIG. 17 shows the cyclic voltammogram of 0.20 mM $Ru(4,4'-Me_2-bpy)_3^{2+}$ in 50 mM sodium phosphate buffer (ph 7) with 0.7 M NaCl at a scan rate of 25 mV/s. Curve (A) represents $Ru(4,4'-Me_2-bpy)_3^{2+}$ alone. Curve (B) represents $Ru(4,4'-Me_2-bpy)_3^{2+}$ in the presence of 0.70 mM 6-mercaptoguanosine 5'-monophosphate.

The results of the cyclic voltammogram are set forth graphically in FIG. 17, where curve A shows Ru(4,4'-Me$_2$-bpy)$_3^{2+}$ alone (4,4'-Me$_2$-bpy=4,4'-'dimethyl-2,2'-bipyridine). Upon addition of 5'-GMP, no enhancement of the Ru(Me$_2$bpy)$_3^{2+}$ wave is observed; however, addition of 6-mercaptoguanosine 5'-monophosphate (6-S-GMP) leads to a dramatic current enhancement (curve B). The peak current in the presence of 5'-GMP is identical to that in curve A. The data demonstrate that it is possible to detect 6-mercaptoguanine bases in the presence of background native guanine.

EXAMPLE 11

Detection of DNA Hybridization with the Preselected Base on the Target Strand

Nylon membranes (Hybond N+, Amersham, 480–600 μg/cm$^2$) are cut into circular shapes, approximately 6 mm in diameter. The nylon disks are placed in a concentrated solution of polycytidylic acid (available from Sigma) in water and allowed to soak for 1 hour. The disks are then removed from the polycytidylic acid (poly[C]) solution and placed on parafilm and allowed to dry. As the disks are drying, an additional 15 μL of poly[C] solution is added to the films in three 5 μL aliquots. The disks are allowed to dry completely. The dried nylon disks are then washed in the low salt buffer (50 mM Na-phosphate, pH=6.8, [Na$^+$]=80 mM) to remove any poly[C] which is not strongly bound during the soaking process.

As a control experiment, a poly[C]-impregnated disk is put through a mock hybridization procedure in which it is not exposed to any additional nucleic acid, but is exposed to all other hybridization steps. The disk is placed in 400 μL of milli-Q water, heated at 48° C. for 1 hour, and allowed to cool to room temperature. The disk is removed from the water and washed in low salt buffer prior to electrochemical analysis. Disks prepared in this manner represent the background scans (A) in both FIGS. 18 and 19.

A poly[C]-impregnated disk is placed in 400 μL of a polyguanylic acid (available from Sigma) in water solution, heated at 48° C. for 1 hour, and allowed to cool to room temperature. The disk is then removed from the polyguanylic acid (poly[G]) solution and washed in a low salt buffer prior to electrochemical analysis.

Calf thymus DNA (available from Sigma) in water is denatured (melted) by heating to 90° C. for 10 minutes. A poly[C]-impregnated disk is placed in the denatured calf thymus DNA solution, heated to 48° C. for 1 hour, and allowed to cool to room temperature. The disk is removed from the calf thymus DNA solution and washed in low salt buffer prior to electrochemical analysis. As a control, a nylon disk which has not been impregnated with poly[C] is also subjected to the same procedure. Binding and detection of calf thymus DNA by adsorption into the nylon film (not by hybridization) is observed in the control membrane.

The nylon disk, treated as described above, is inserted into the electrochemical cell, after the conditioning of the ITO electrode with the low salt buffer. 200 μL of a 200 μM Ru(bpy)$_3^{2+}$ solution is pipetted into the cell and a cyclic voltammogram is taken after a 15 minute equilibration time. The scan rate is 25 mV/sec.

Figure 18:
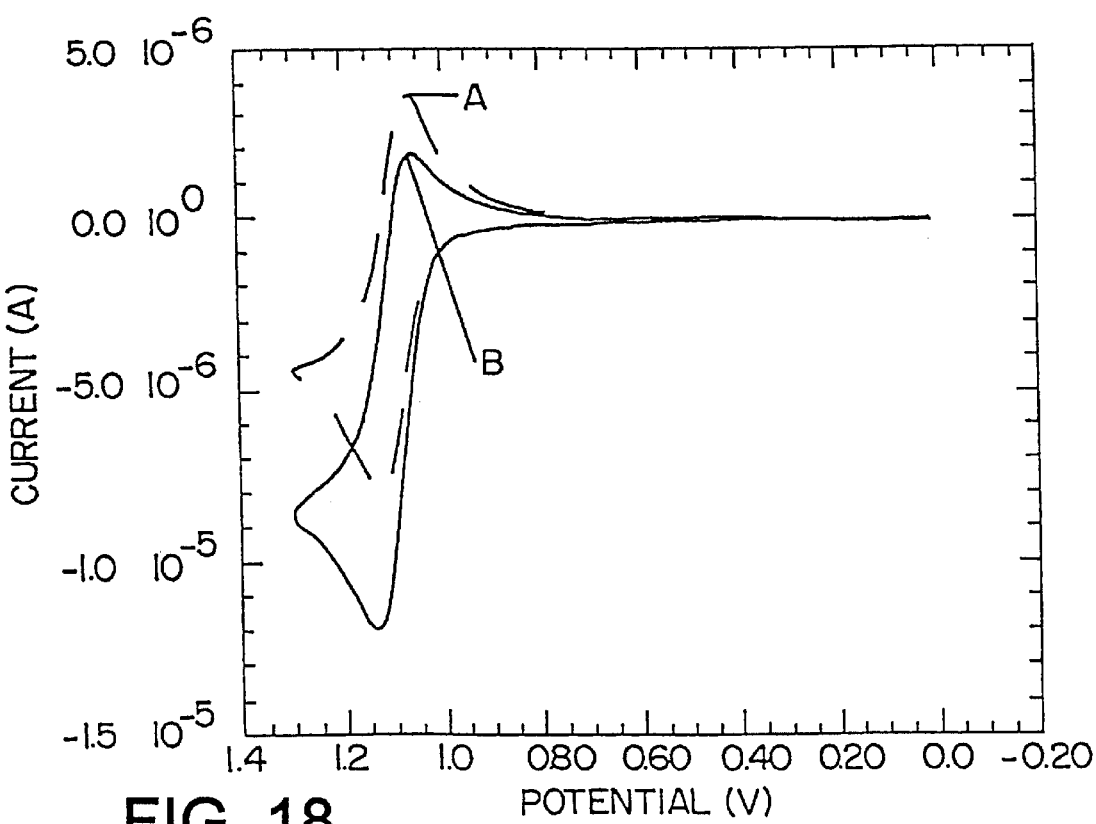
FIG. 18 shows cyclic voltammograms of 200 $\mu$M of $Ru(bpy)_3^{2+}$ at ITO working electrodes to which a Hybond N+ nylon membrane is attached. Membranes are impregnated with poly[C] and subjected to the hybridization protocol in buffer (A) and a concentrated solution of poly[G] (B).
Figure 19:
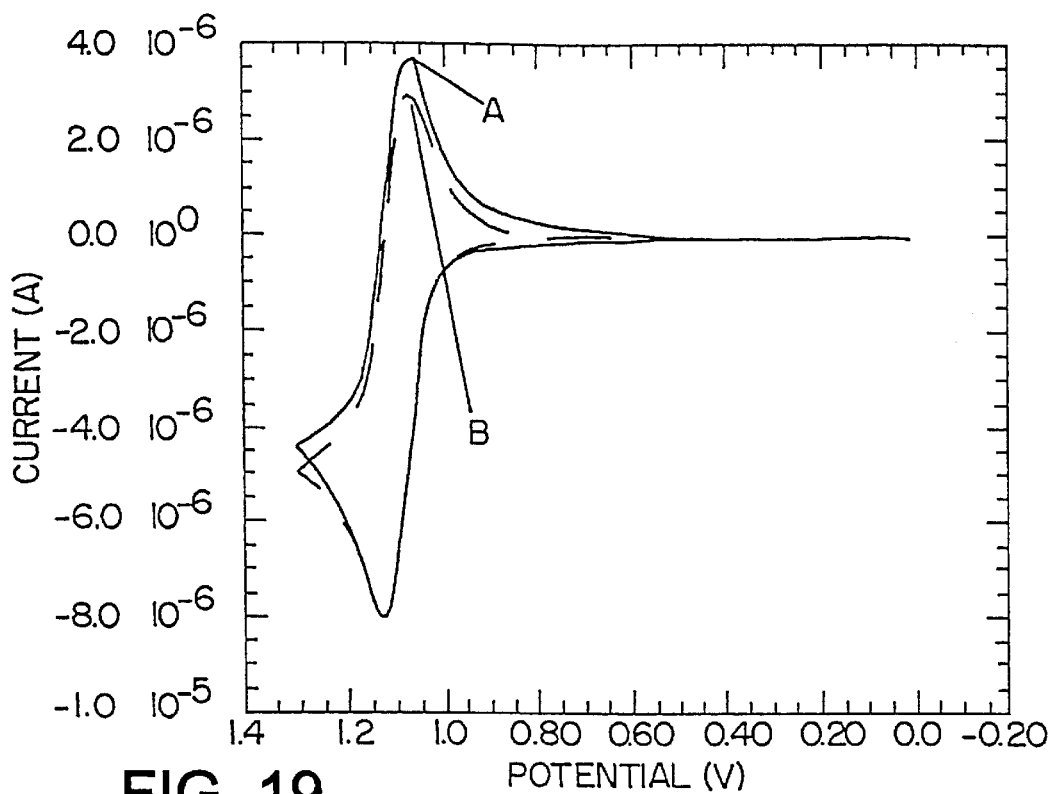
FIG. 19 shows cyclic voltammograms of 200 $\mu$M of $Ru(bpy)_3^{2+}$ at ITO working electrodes to which a Hybond N+ nylon membrane is attached. Membranes are impregnated with poly[C] and subjected to the hybridization protocol in buffer (A) and a concentrated solution of denatured calf thymus DNA (B).

The cyclic voltammogram is reported in FIG. 18. The probe sequence poly[C] is immobilized onto a Hybond N+ nylon membrane and the hybridization protocol is carried out in buffer ("mock hybridization"). The membrane is attached to the ITO working electrode and a cyclic voltammogram of Ru(bpy)$_3^{2+}$ is obtained (A). The membrane is immersed in a solution of poly[G] and hybridization is performed according to the same protocol. The cyclic voltammogram of Ru(bpy)$_3^{2+}$ is then measured (B), and a large current enhancement is obtained due to catalytic oxidation of the hybridized poly[G] target. As shown in FIG. 19, the assay is specific for the appropriate sequence. FIG. 19 compares the voltammetry for the poly[C] membrane where the hybridization procedure was carried out in buffer (A) or in a solution of single-stranded calf thymus DNA (B). FIG. 19 shows that if the target sequence is not present, no current enhancement is obtained.

EXAMPLE 12

Detection of DNA at Nylon-Modified Glassy Carbon Electrodes

Figure 20:
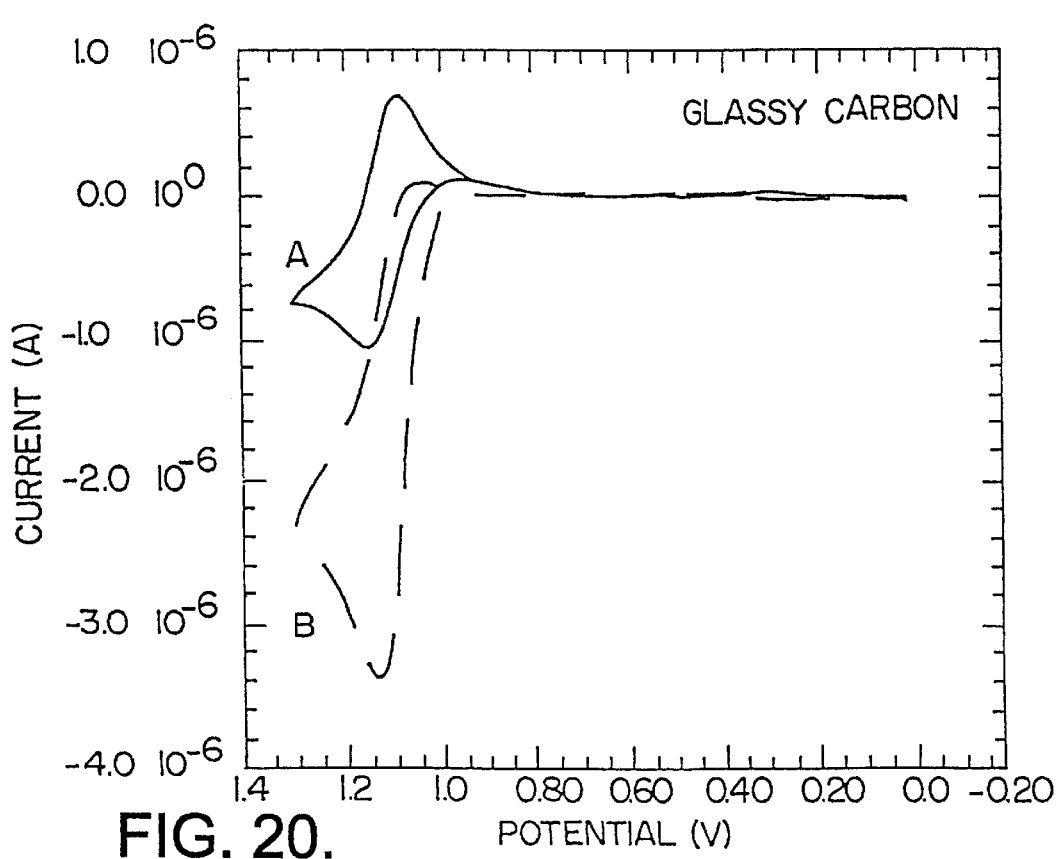
FIG. 20 shows the cyclic voltammograins (scan rate=25 mV/s) of 200 $\mu$M $Ru(bpy)_3^{2+}$ at a nylon-modified glassy carbon electrode (A) without DNA or (B) after adsorption of DNA to the nylon film.

FIG. 20 shows the cyclic voltammogram (or "CV") of a glassy carbon electrode with a nylon film attached before (A) and after (B) immobilization of DNA on the nylon film.

Nylon membrane (Zeta-Probe, Bio-Rad, 80–100 μg/cm$^2$) was cut into circular shapes, approximately 5 mm in diameter. The nylon disk as fashioned covers the glassy carbon electrode surface and is held in position by a plastic sleeve. For the experiments in which only the CV of the metal complex was obtained, the glassy carbon electrode was first conditioned with a low salt, 50 mM Na-phosphate buffer (pH=6.8, [Na$^+$]=80 mM). The nylon disk (no DNA) was then attached to the electrode and 400 μL of a 200 μM Ru(bpy)$_3^{2+}$ solution was pipetted into the electrochemical cell. An equilibration time of 15 minutes was used prior to electrochemical analysis. Cyclic voltammograms were collected using an PAR 273A potentiostat using a scan rate of 25 mV/s. In a typical DNA experiment, the glassy carbon electrode is first conditioned in the low salt, Na-phosphate buffer. A nylon disk was soaked for approximately 5 minutes in a solution of 5.8 mM calf thymus DNA dissolved in water. The disk was then removed from the solution and positioned over the glassy carbon electrode using the sleeve to hold it in place. 400 μL of a 200 μM (Ru(bpy)$_3^{2+}$ was pipetted into the electrochemical cell and after a 15 minute equilibration a cyclic voltammogram was taken using a scan rate of 25 mV/s.

The foregoing is illustrative of the present invention and is not to be construed as limiting thereof. The invention is defined by the following claims, with equivalents of the claims to be included therein.

That which is claimed is:

1. A method of detecting DNA hybridization comprising:
   (a) contacting a DNA sample with an oligonucleotide probe to form a hybridized DNA;
   (b) reacting said hybridized DNA with a transition metal complex that oxidizes a preselected base in said oligonucleotide probe in an oxidation-reduction reaction under conditions that cause an oxidation-reduction reaction between the transition metal complex and the preselected base, said oligonucleotide probe having at least one of said preselected bases, from which preselected base there is electron transfer to the transition metal complex, resulting in regeneration of the reduced form of the transition metal complex as part of a catalytic cycle;
   (c) detecting said oxidation-reduction reaction;
   (d) determining the presence or absence of hybridized DNA from said detected oxidation-reduction reaction at said preselected base.

2. The method according to claim 1, wherein said determining step further comprises the steps of: (i) measuring the reaction rate of said detected oxidation-reduction reaction, (ii) comparing said measured reaction rate to the oxidation-reduction reaction rate of the transition metal complex with a single-stranded DNA; and then (iii) determining whether said measured reaction rate is essentially the same as the oxidation-reduction reaction rate of the transition metal complex with single-stranded DNA.

3. The method according to claim 1, wherein said DNA sample is a single-stranded DNA sample, and said hybridized DNA is a duplex.

4. The method according to claim 1, wherein said oligonucleotide probe includes from about 4 to about 100 bases.

5. The method according to claim 1, wherein said preselected base is guanine.

6. The method according to claim 1, wherein said preselected base is adenine.

7. The method according to claim 1, wherein said transition metal complex is selected from the group consisting of Ru(bpy)$_3^{2+}$, Ru(Me$_2$-bpy)$_3^{2+}$, Ru(Me$_2$-phen)$_3^{2+}$, Fe(bpy)$_3^{2+}$, Fe(5-Cl-phen)$_3^{2+}$, Os(bpy)$_3^{2+}$, Os(5-Cl-phen)$_3^{2+}$, and ReO$_2$(py)$_4^{1+}$.

8. The method according to claim 1, wherein said reacting step comprises reacting said transition metal complex with said hybridized DNA sample under conditions sufficient to effect the selective oxidation of said preselected base.

9. The method according to claim 1, further comprising the step of amplifying said hybridized DNA prior to said contacting step.

10. The method according to claim 9, wherein said step of amplifying said DNA sample is carried out by polymerase chain reaction, strand displacement amplification, ligase chain reaction, or nucleic acid sequence-based amplification.

11. The method according to claim 2, wherein said step of measuring the reaction rate of said oxidation-reduction reaction comprises measuring the cyclic voltammogram of the reaction.

12. The method according to claim 2, wherein said step of comparing comprises comparing the cyclic voltammogram of the reaction of the transition metal complex with the hybridized DNA sample against the known cyclic voltammogram of the reaction of the transition metal complex with single-stranded DNA.

13. The method according to claim 1, wherein said oligonucleotide probe is immobilized on a solid surface.

14. The method according to claim 13, wherein said transition metal complex is immobilized on said solid surface.

15. A method of sequencing DNA comprising
   (a) contacting a DNA sample with an oligonucleotide probe to form a hybridized DNA, said oligonucleotide probe including a preselected base having a unique oxidation rate;
   b) reacting said hybridized DNA with a transition metal complex that oxidizes said preselected base in said oligonucleotide probe in an oxidation-reduction reaction under conditions that cause an oxidation-reduction reaction between the transition metal complex and the preselected base, said oligonucleotide probe having a predetermined number of said preselected base, from which preselected base there is electron transfer to the transition metal complex, resulting in regeneration of the reduced form of the transition metal complex as part of a catalytic cycle;

(c) detecting said oxidation-reduction reaction;

(d) measuring the reaction rate of said detected oxidation-reduction reaction; and (e) identifying the base paired with said preselected base.

16. The method according to claim 15, wherein said identifying step comprises (i) comparing said measured reaction rate to each of the four different known oxidation-reduction reaction rates of the transition metal complex with a DNA having adenine, cytosine, guanine, or thymine bound to said preselected base; and (ii) determining which of said known oxidation-reduction reaction rates is essentially the same as said measured reaction rate.

17. The method according to claim 15, wherein said oligonucleotide probe further includes a second preselected base having a unique oxidation rate, wherein the oxidation rate of said second preselected base is different from the oxidation rate of said preselected base.

18. The method according to claim 17, wherein said detecting step further comprises detecting the oxidation-reduction reaction of the transition metal complex with said second preselected base; wherein said measuring step further comprises measuring the reaction rate of said detected oxidation-reduction reaction of the transition metal complex with said second preselected base; and wherein said identifying step further comprises identifying the base paired with said second preselected base.

19. The method according to claim 15, further comprising repeating steps (a) through (e) with a sufficient number of oligonucleotide probes having said preselected base at different sites to identify each base in said DNA sample.

20. A method of detecting RNA hybridization comprising:

(a) contacting an RNA sample with an oligonucleotide probe to form a hybridized RNA;

(b) reacting said hybridized RNA with a transition metal complex that oxidizes a preselected base in said oligonucleotide probe in an oxidation-reduction reaction under conditions that cause an oxidation-reduction reaction between the transition metal complex and the preselected base, said oligonucleotide probe having at least one of said preselected base, from which preselected base there is electron transfer to the transition metal complex, resulting in regeneration of the reduced form of the transition metal complex as part of a catalytic cycle;

(c) detecting said oxidation-reduction reaction;

(d) determining the presence or absence of hybridized RNA from said detected oxidation-reduction reaction at said preselected base.

21. The method according to claim 20, wherein said determining step further comprises the steps of: (i) measuring the reaction rate of said detected oxidation-reduction reaction, (ii) comparing said measured reaction rate to the oxidation-reduction reaction rate of the transition metal complex with a single-stranded RNA; and then (iii) determining whether said measured reaction rate is essentially the same as the oxidation-reduction reaction rate of the transition metal complex with single-stranded RNA.

22. The method according to claim 20, wherein said RNA sample is a single-stranded RNA sample, and said hybridized RNA is a duplex.

23. The method according to claim 20, wherein said oligonucleotide probe includes from about 4 to about 100 bases.

24. The method according to claim 20, wherein said preselected base is guanine.

25. The method according to claim 20, wherein said preselected base is adenine.

26. The method according to claim 20, wherein said transition metal complex is selected from the group consisting of $Ru(bpy)_3^{2+}$, $Ru(Me_2-bpy)_3^{2+}$, $Ru(Me_2-phen)_3^{2+}$, $Fe(bpy)_3^{2+}$, $Fe(5-Cl-phen)_3^{2+}$, $Os(bpy)_3^{2+}$, $Os(5-Cl-phen)_3^{2+}$, and $ReO_2(py)_4^{1+}$.

27. The method according to claim 20, wherein said reacting step comprises reacting said transition metal complex with said hybridized RNA sample under conditions sufficient to effect the selective oxidation of said preselected base.

28. The method according to claim 20, further comprising the step of amplifying said hybridized RNA prior to said contacting step.

29. The method according to claim 28, wherein said step of amplifying said RNA sample is carried out by reverse-transcriptase polymerase chain reaction.

30. The method according to claim 21, wherein said step of measuring the reaction rate of said oxidation-reduction reaction comprises measuring the cyclic voltammogram of the reaction.

31. The method according to claim 21, wherein said step of comparing comprises comparing the cyclic voltammogram of the reaction of the transition metal complex with the hybridized RNA sample against the known cyclic voltammogram of the reaction of the transition metal complex with single-stranded RNA.

32. The method according to claim 20, wherein said oligonucleotide probe is immobilized on a solid surface.

33. The method according to claim 32, wherein said transition metal complex is immobilized on said solid surface.

34. A method of sequencing RNA comprising:

(a) contacting an RNA sample with an oligonucleotide probe to form a hybridized RNA, said oligonucleotide probe including a preselected base having a unique oxidation rate;

(b) reacting said hybridized RNA with a transition metal complex that oxidizes said preselected base in said oligonucleotide probe in an oxidation-reduction reaction under conditions that cause an oxidation-reduction reaction between the transition metal complex and the preselected base, said oligonucleotide probe having a predetermined number of said preselected base, from which preselected base there is electron transfer to the transition metal complex, resulting in regeneration of the reduced form of the transition metal complex as part of a catalytic cycle;

(c) detecting said oxidation-reduction reaction;

(d) measuring the reaction rate of said detected oxidation-reduction reaction; and (e) identifying the base paired with said preselected base.

35. The method according to claim 34, wherein said identifying step comprises (i) comparing said measured reaction rate to each of the four different known oxidation-reduction reaction rates of the transition metal complex with an RNA having adenine, cytosine, guanine, or uracil bound to said preselected base; and (ii) determining which of said known oxidation-reduction reaction rates is essentially the same as said measured reaction rate.

36. The method according to claim 34, wherein said oligonucleotide probe further includes a second preselected base having a unique oxidation rate, wherein the oxidation rate of said second preselected base is different from the oxidation rate of said preselected base.

37. The method according to claim 36, wherein said detecting step further comprises detecting the oxidation-reduction reaction of the transition metal complex with said second preselected base; wherein said measuring step further comprises measuring the reaction rate of said detected oxidation-reduction reaction of the transition metal complex with said second preselected base; and wherein said identifying step further comprises identifying the base paired with said second preselected base.

38. The method according to claim 34, further comprising repeating steps (a) through (e) with a sufficient number of oligonucleotide probes having said preselected base at different sites to identify each base in said RNA sample.

39. A method of detecting a nucleic acid, said nucleic acid containing at least one preselected base, said method comprising:
(a) reacting said nucleic acid with a transition metal complex that oxidizes said preselected base in an oxidation-reduction reaction under conditions that cause an oxidation-reduction reaction between the transition metal complex and the preselected base, from which preselected base there is electron transfer to the transition metal complex, resulting in regeneration of the reduced form of the transition metal complex as part of a catalytic cycle;
(b) detecting said oxidation-reduction reaction; and
(c) determining the presence or absence of said nucleic acid from said detected oxidation-reduction reaction at said preselected base.

40. A method according to claim 39, wherein said reacting step is preceded by the step of:
contacting said nucleic acid with a complementary nucleic acid to form a hybridized nucleic acid.

41. The method according to claim 40, wherein said determining step further comprises the steps of: (i) measuring the reaction rate of said detected oxidation-reduction reaction, (ii) comparing said measured reaction rate to the oxidation-reduction reaction rate of the transition metal complex with a single-stranded nucleic acid; and then (iii) determining whether said measured reaction rate is essentially the same as the oxidation-reduction reaction rate of the transition metal complex with single-stranded nucleic acid.

42. The method according to claim 41, wherein said step of measuring the reaction rate of said oxidation-reduction reaction comprises measuring the cyclic voltammogram of the reaction.

43. The method according to claim 41, wherein said step of comparing comprises comparing the cyclic voltammogram of the reaction of the transition metal complex with the hybridized nucleic acid sample against the known cyclic voltammogram of the reaction of the transition metal complex with single-stranded nucleic acid.

44. The method according to claim 39, wherein said nucleic acid includes from about 4 to about 100 bases.

45. The method according to claim 39, wherein said preselected base is selected from the group consisting of guanine and adenine.

46. The method according to claim 39, wherein said transition metal complex is selected from the group consisting of $Ru(bpy)_3^{2+}$, $Ru(Me_2\text{-}bpy)_3^{2+}$, $Ru(Me_2\text{-}phen)_3^{2+}$, $Fe(bpy)_3^{2+}$, $Fe(5\text{-}Cl\text{-}phen)_3^{2+}$, $Os(bpy)_3^{2+}$, $Os(5\text{-}Cl\text{-}phen)_3^{2+}$, and $ReO_2(py)_4^{1+}$.

47. A method according to claim 39, wherein said nucleic acid is DNA.

48. A method according to claim 39, wherein said nucleic acid is RNA.

49. The method according to claim 39, further comprising the step of amplifying said nucleic acid prior to said reacting step.

50. The method according to claim 49, wherein said step of amplifying said nucleic acid is carried out by polymerase chain reaction, strand displacement amplification, ligase chain reaction, or nucleic acid sequence-based amplification.

51. The method according to claim 39, wherein said nucleic acid is immobilized on a solid surface.

52. The method according to claim 51, wherein said transition metal complex is immobilized on said solid surface.

53. A method of detecting the presence or absence of a target nucleic acid in a test sample suspected of containing the same, wherein said target nucleic acid contains at least one preselected base, said method comprising:
(a) contacting said test sample to an oligonucleotide probe that specifically binds to said target nucleic acid to form a hybridized nucleic acid;
(b) contacting said hybridized nucleic acid to a transition metal complex that oxidizes said preselected base in an oxidation-reduction reaction under conditions that cause an oxidation-reduction reaction between the transition metal complex and the preselected base, from which preselected base there is electron transfer to the transition metal complex, resulting in regeneration of the reduced form of the transition metal complex as part of a catalytic cycle;
(c) detecting the presence or absence of said oxidation-reduction reaction associated with said hybridized nucleic acid; and
(d) determining the presence or absence of said target nucleic acid in said test sample from said detected oxidation-reduction reaction at said preselected base.

54. A method according to claim 53, further comprising the step of:
separating said test sample from said hybridized nucleic acid prior to said detecting step.

55. A method according to claim 53, wherein said target nucleic acid is longer than said oligonucleotide probe, and wherein at least one of said preselected base is not hybridized to said oligonucleotide probe in said hybridized nucleic acid.

56. A method according to claim 54, wherein said determining step is a quantiatively determining step.

57. The method according to claim 54, wherein said determining step further comprises the steps of: (i) measuring the reaction rate of said detected oxidation-reduction reaction, (ii) comparing said measured reaction rate to the oxidation-reduction reaction rate of the transition metal complex with a single-stranded target nucleic acid; and then (iii) determining whether said measured reaction rate is essentially the same as the oxidation-reduction reaction rate of the transition metal complex with single-stranded target nucleic acid.

58. The method according to claim 57, wherein said step of measuring the reaction rate of said oxidation-reduction reaction comprises measuring the cyclic voltammogram of the reaction.

59. The method according to claim 57, wherein said step of comparing comprises comparing the cyclic voltammogram of the reaction of the transition metal complex with the hybridized target nucleic acid sample against the known cyclic voltammogram of the reaction of the transition metal complex with single-stranded target nucleic acid.

60. The method according to claim 53, wherein said target nucleic acid includes from about 4 to about 100 bases.

61. The method according to claim 53, wherein said preselected base is selected from the group consisting of guanine and adenine.

62. The method according to claim 53, wherein said transition metal complex is selected from the group consisting of $Ru(bpy)_3^{2+}$, $Ru(Me_2\text{-bpy})_3^{2+}$, $Ru(Me_2\text{-phen})_3^{2+}$, $Fe(bpy)_3^{2+}$, $Fe(5\text{-Cl-phen})_3^{2+}$, $Os(bpy)_3^{2+}$, $Os(5\text{-Cl-phen})_3^{2+}$, and $ReO_2(py)_4^{1+}$.

63. A method according to claim 53, wherein said target nucleic acid is DNA.

64. A method according to claim 53, wherein said target nucleic acid is RNA.

65. The method according to claim 53, further comprising the step of amplifying said target nucleic acid prior to said reacting step.

66. The method according to claim 65, wherein said step of amplifying said target nucleic acid sample is carried out by polymerase chain reaction, strand displacement amplification, ligase chain reaction, or nucleic acid sequence-based amplification.

67. The method according to claim 53, wherein said oligonucleotide probe is immobilized on a solid surface.

68. The method according to claim 67, wherein said transition metal complex is immobilized on said solid surface.

69. The method according to claim 40, wherein the preselected base is selected from the group consisting of guanine, adenine, 6-mercaptoguanine, 8-oxo-guanine, and 8-oxo-adenine.

70. A method according to claim 69, wherein said reacting step is preceded by the step of:
    contacting said nucleic acid with a complementary nucleic acid to form a hybridized nucleic acid.

71. A method of detecting a nucleic acid, said nucleic acid containing at least one preselected base, said method comprising:
    (a) contacting a sample containing said nucleic acid to an electrode, said electrode comprising (i) a conductive substrate having a working surface formed thereon; and (ii) a nonconductive polymer layer connected to said working surface, wherein said polymer layer binds said nucleic acid thereto;
    (b) reacting said nucleic acid with a transition metal complex that oxidizes said preselected base in an oxidation-reduction reaction under conditions that cause an oxidation-reduction reaction between the transition metal complex and the preselected base, from which preselected base there is electron transfer to the transition metal complex, resulting in regeneration of the reduced form of the transition metal complex as part of a catalytic cycle, and wherein said polymer layer is porous to said transition metal complex;
    (c) detecting said oxidation-reduction reaction by measuring current flow through said electrode; and
    (d) determining the presence or absence of said nucleic acid from said detected oxidation-reduction reaction at said preselected base.

72. A method according to claim 71, wherein said reacting step is preceded by the step of:
    contacting said nucleic acid with a complementary nucleic acid to form a hybridized nucleic acid.

73. The method according to claim 69, wherein said determining step is a quantitatively determining step.

74. The method according to claim 69, wherein said nucleic acid is DNA.

75. The method according to claim 69, wherein said nucleic acid is RNA.

76. The method according to claim 69, wherein said preselected base is selected from the group consisting of guanine and adenine.

77. The method according to claim 69, wherein said transition metal complex is selected from the group consisting of $Ru(bpy)_3^{2+}$, $Ru(Me_2\text{-bpy})_3^{2+}$, $Ru(Me_2\text{-phen})_3^{2+}$, $Fe(bpy)_3^{2+}$, $Fe(5\text{-Cl-phen})_3^{2+}$, $Os(bpy)_3^{2+}$, $Os(5\text{-Cl-phen})_3^{2+}$, and $ReO_2(py)_4^{1+}$.

78. The method according to claim 71, wherein said determining step is a quantitatively determining step.

79. The method according to claim 71, wherein said nucleic acid is DNA.

80. The method according to claim 71, wherein said nucleic acid is RNA.

81. The method according to claim 71, wherein said preselected base is selected from the group consisting of guanine and adenine.

82. The method according to claim 71, wherein said transition metal complex is selected from the group consisting of $Ru(bpy)_3^{2+}$, $Ru(Me_2\text{-bpy})_3^{2+}$, $Ru(Me_2\text{-phen})_3^{2+}$, $Fe(bpy)_3^{2+}$, $Fe(5\text{-Cl-phen})_3^{2+}$, $Os(bpy)_3^{2+}$, $Os(5\text{-Cl-phen})_3^{2+}$, and $ReO_2(py)_4^{1+}$.

83. The method according to claim 13 wherein said solid surface comprises an electrode.

84. The method according to claim 15 wherein said detection of said oxidation/reduction reaction in step (c) comprises the use of an electrode.

85. The method according to claim 32 wherein the solid surface comprises an electrode.

86. The method according to claim 34 wherein said detection of said oxidation/reduction reaction in step (c) comprises the use of an electrode.

87. The method according to claim 40 wherein said complementary nucleic acid is immobilized on a solid surface.

88. The method according to claim 87 wherein said solid surface comprises an electrode.

89. The method according to claim 67 wherein said solid surface comprises an electrode.

90. The method according to claim 72 wherein the complementary nucleic acid is immobilized on said polymer layer.

* * * * *

UNITED STATES PATENT AND TRADEMARK OFFICE
CERTIFICATE OF CORRECTION

PATENT NO. : 6,361,951 B1
DATED : March 26, 2002
INVENTOR(S) : Thorp et al.

It is certified that error appears in the above-identified patent and that said Letters Patent is hereby corrected as shown below:

<u>Title page,</u>
Item [56], U.S. PATENT DOCUMENTS, the fourth-listed US Reference should appear as follows -- 4,704,353 --

<u>Column 1,</u>
Lines 15 - 19, the paragraph beginning with "This application is a continuation-in-part" should be omitted.

<u>Column 8,</u>
Line 43, should appear as follows -- chlorophenanthroline)$_3$ ("Fe(5-Cl-phen)$_3^{2+}$"), --
Line 44, should appear as follows -- Osmium 2+(5- --

<u>Column 19,</u>
Line 37, should appear as follows -- Oligonucleotide probes, hybridization methodology, oxi-" --

<u>Column 34,</u>
Line 50, should read as follows -- 56. A method according to claim 53, wherein said deter- --
Line 52, should read as follows -- 57. The method according to claim 53, wherein said --

Signed and Sealed this

Fifth Day of August, 2003

JAMES E. ROGAN
*Director of the United States Patent and Trademark Office*